United States Patent [19]

Rodriguez et al.

[11] Patent Number: 5,591,629
[45] Date of Patent: Jan. 7, 1997

[54] MONOCLONAL ANTIBODIES WHICH PROMOTE CENTRAL NERVOUS SYSTEM REMYELINATION

[75] Inventors: Moses Rodriguez; David J. Miller, both of Rochester, Minn.

[73] Assignee: Mayo Foundation for Medical Education & Research, Rochester, Minn.

[21] Appl. No.: 236,520

[22] Filed: Apr. 29, 1994

[51] Int. Cl.$^6$ .............................. C07K 16/28; C12N 5/12
[52] U.S. Cl. .................................. 435/240.27; 435/70.21; 530/388.2; 530/809; 530/839; 530/863
[58] Field of Search ............................. 435/240.27, 70.21; 530/388.2, 809, 839, 863

[56] References Cited

FOREIGN PATENT DOCUMENTS

92/94442  3/1992  WIPO .

OTHER PUBLICATIONS

Miller, D. M. and Rodriguez, M., "A Monoclonal Autoantibody That Promotes Central Nervous System Remyelination in a Model of Multiple Sclerosis is a Natural Autoantibody Encoded by Germline Immunoglobulin Genes," *J. of Immunology,* 154(5):2460–2469 (1995).
Miller, D. M. et al., "Monoclonal Autoantibodies Promote Central Nervous System Repair in an Animal Model of Multiple Sclerosis," *J. of Neuroscience,* 14(10):6230–6238 (1994).
Rodriguez, M. and Miller, D. J., "Immune Promotion of Central Nervous system Remyelination," *Progress in Brain Research,* 103:343–355 (1994).
Roitt (1991) "Essential Immunology", Blackwell Scientific Publications, Oxford, pp. 65–68 & 74.
Goding (1983) "Monoclonal Antibodies", Academic Press, Orlando, pp. 56–91.
Bansal R., et al., "Stimulation of Oligodendrocyte Differentiation in Culture by Growth in the Presence of a Monoclonal Antibody to Sulfated Glycolipid," *J. Neuro. Res.,* 21:260–267 (1988).
Patick, A. K., et al., "Persistence of Theiler's Virus Infection Following Promotion of Central Nervous System Remyelination," *J. of Neuropath. and Exp. Neurology,* 50(5):523–537 (1991).
Rodriguez, M. and Lindsley, M. D., "Immunosuppression Promotes CNS Remyelination in Chronic Virus–Induced Demyelinating Disease," *Neurology,* 42(2):348–357 (1992).
Miller, D. J., et al., "Monoclonal Antibodies Stimulate Remyelination in a Viral Model of Multiple Sclerosis," *J. Neuropathol Exp. Neurol,* vol. 52 Abstract #195 (1993).
Miller, D. J. and Rodriguez, M. R., "The Beneficial Effect of Autoantibodies in Response to Central Nervous System Demyelination," *Abstract for Gordon Conference on Myelin,* Marach 13–18, 1994, Casa Serena, Oxnard, CA.
Bansal R., and Pfeiffer, S. E., "Reversible Inhibition of Oligodendrocyte Progenitor Differentiation by a Monoclonal Antibody Against Surface Galactolipidss," *Proc. Natl. Acad. Sci. USA,* 86:6181–6185 (1989).

Rodriguez, M., "Central Nervous System Demyelination and Remyelination in Multiple Sclerosis and Viral Models of Disease," *J. Neuroimmunology,* 40:255–264 (1992).
Prayoonwiwat, N. and Rodriguez, M,. "The Potential for Oligodendrocyte Proliferation During Demyelinating Disease," *J. Neuropathology and Exp. Neurology,* 51(1):55–63 (1993).
Rodriguez, M., et al., "Remyelination by Oligodendrocytes Stimulated by Antiserum to Spinal Cord," *J. Neuropathology and Exp. Neurology,* 46(1):84–95 (1987).
Rodriguez, M. D. and Lennon, V. A., "Immunoglobulins Promote Remyelination in the Central Nervous System," *Anals. of Neurology,* 27(1):12–17 (1990).
Rodriguez, M., et al., "Immunoglobulins Stimulate Central Nervous System Remyelination: Electron Microscopic and Morphometric Analysis of Proliferation Cells," *Laboratory Investigation,* 64(3):358–370 (1991).
Kabat, E. A., et al., "The Rapid Production of Acute Disseminated Encephalomyelitis in Rhesus Monkeys by Injection of Heterologous and Homologous Brain Tissue with Adjuvants," *J. Exp. Med.,* 85:117–129 (1947).
Raine, C. S., et al., "Antiserum–Induced Dissociation of Myelinogenesis In Vitro," *Laboratory Investigation,* 38(4):397–403 (1978).
Lehrer, G. V., et al., "Stimulation of Myelin Lipid Synthesis In Vitro by White Matter Antiserum in Absence of Complement," *Brain Research,* 172:557–570 (1979).
Weiner, H. L., et al., "Double–Blind Pilot Trial of Oral Tolerization with Myelin Antigens in Multiple Sclerosis," *Science,* 259:1321–1324 (1993).
Hafler, D. A., and Weiner, H. L., "MS: A CNS and Systemic Autoimmune Disease," *Immunology Today,* 10(3):104–107 (1989).
Steinman, L., "The Development of Rational Strategies for Selective Immunotherapy Against Autoimmune Demyelinating Disease," *Advances in Immunology,* 49:357–379 (1991).
Martin, R., et al., "Immunological Aspects of Demyelinating Diseases," *Annu. Rev. Immunol.,* 10:153–187 (1992).
Benjamins, J. A. and Dyer, C. A., "Glycolipids and Transmembrane Signaling in Oligodendroglia," *Ann. NY Acad. Sci.,* 605:90–100 (1990).
Olsson, T., "Immunology of Multiple Sclerosis," *Curr. Opin. in Neurology and Nurosurgery,* 5:195–202 (1992).
Dyer, C. A., "Novel Oligodendrocyte Transmembrane Signaling Systems," *Mol Neurobiol.,* 7(1):1–22 (1993).
Goodkin, D. E., et al., "Experimental Therapies for Multiple Sclerosis: Current Status," *Cleveland Clinic J. of Medicine,* 59(1):63–73 (1992).

(List continued on next page.)

*Primary Examiner*—Paula K. Hutzell
*Assistant Examiner*—Patricia A. Duffy
*Attorney, Agent, or Firm*—Klauber & Jackson

[57] ABSTRACT

Monoclonal IgM antibodies which promote central nervous system remyelination when given to a mammal afflicted with a demyelinating disease are disclosed. These antibodies show multi-organ autoreactivity, and recognize both surface and cytoplasmic determinants on glial cells.

2 Claims, 18 Drawing Sheets

OTHER PUBLICATIONS

Rice, G. P. A., "Virus–Induced Demyelination in Man: Models for Multiple Sclerosis," *Current Opinion in Neurology and Neurosurgery*, 5:188–194 (1992).

Lublin, F. D., "Relapsing Experimental Allergic Encephalomyelitis An Autoimmune Model of Multiple Sclerosis," *Springer Semin in Immunopath.*, 8:197–208 (1985).

Lampert, P. W.,"Autoimmune and Virus–Induced Demyelinating Diseases," *American J. Pathology*, 91(1):176–208 (1978).

Dal Canto, M. C. and Rabinowitz, S. G., "Experimental Models of Virus–Induced Demyelination of the Central Nervous System," *Annals of Neurology*, 11(2):109–127 (1982).

Del Canto, M. C., "Animal Model of Human Disease," *Amer. J. Pathology*, 88:497–500 (1977).

Matthews, W. B., et al., "The Epidemiology of Multiple Sclerosis," In *McAlphine's Multiple Sclerosis*, (NY: Churchill Livingstone), pp. 301–319 (1991).

Matthews, W. B., et al., "The Epidemiology of Multiple Sclerosis," In *McAlphine's Multiple Sclerosis*, (NY: Churchill Livingstone), pp. 3–40 (1991).

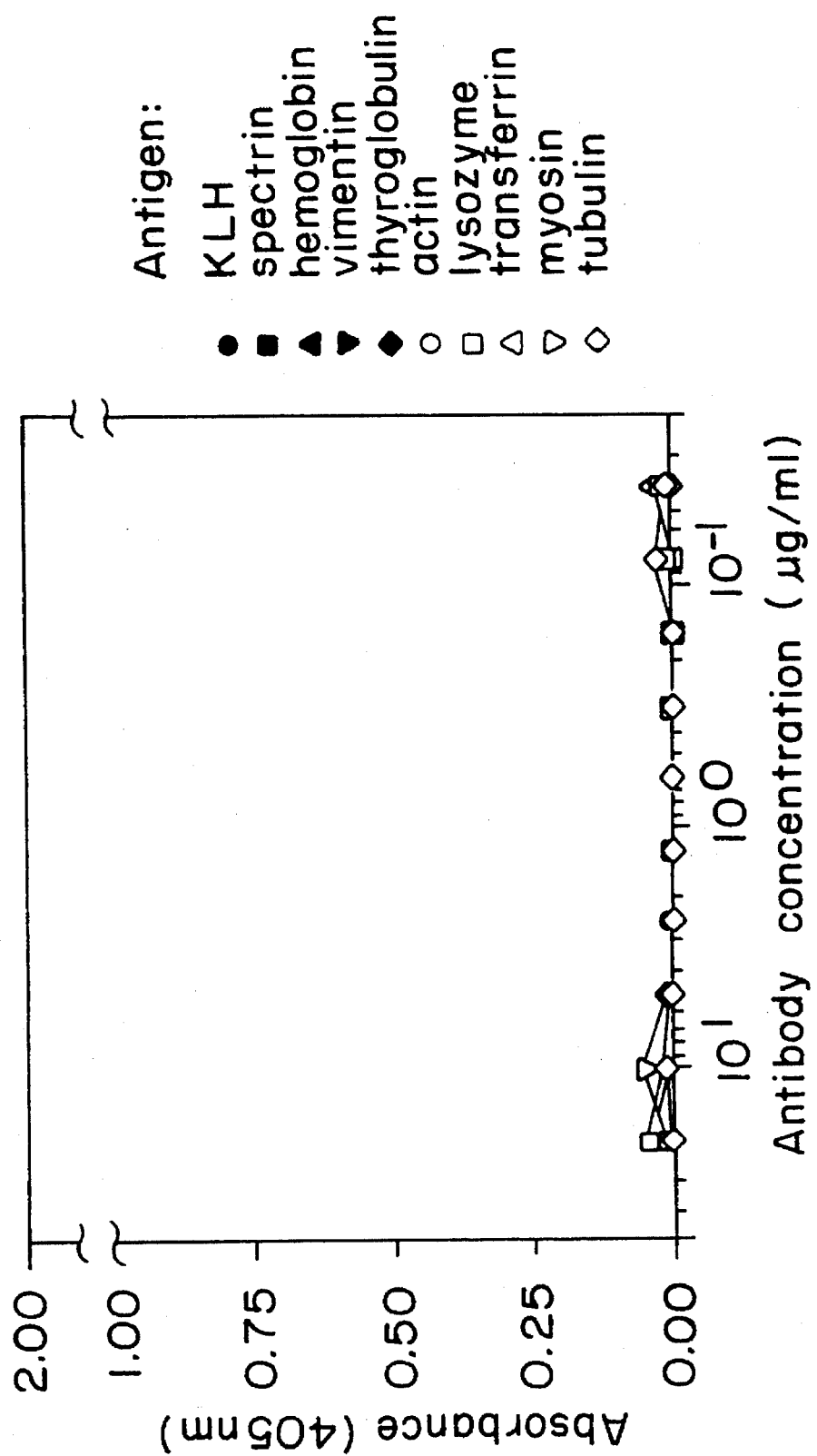

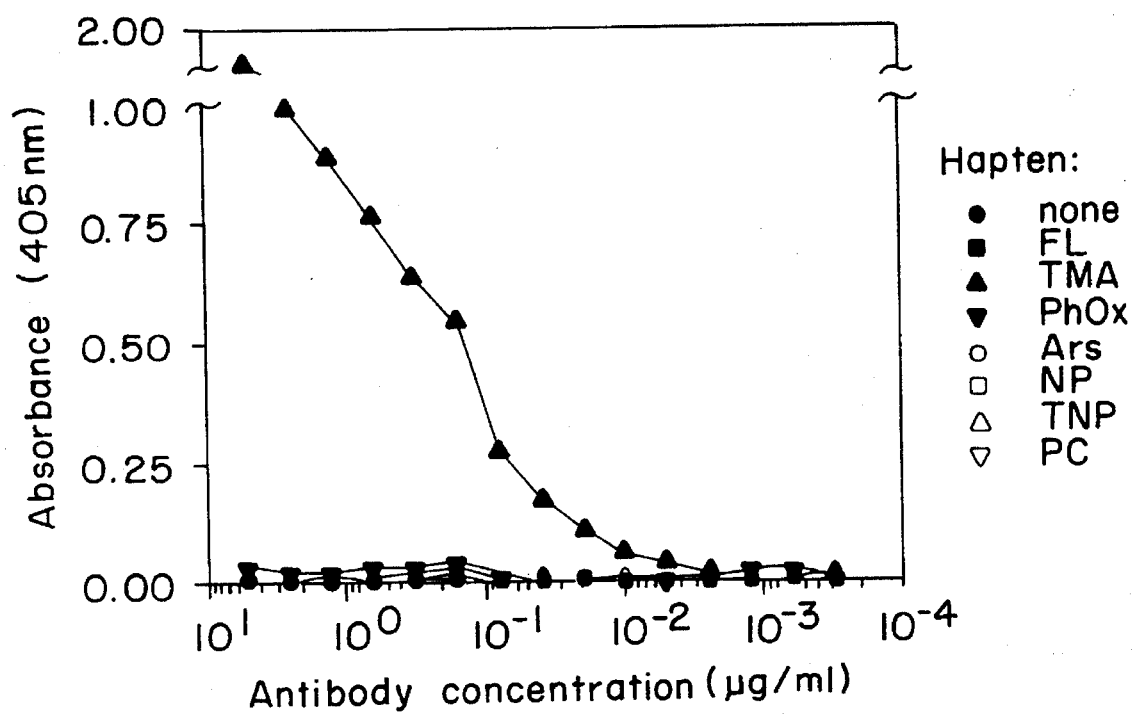

FIG. 11A

Leader region

|  | -19<br>M | G | W | S | C | I | I | L | F | L | V | A | A | A | T | G | V | H | -9<br>S |
|---|---|---|---|---|---|---|---|---|---|---|---|---|---|---|---|---|---|---|---|
| SCH94.03 | ATG | GGA | TGG | AGC | TGT | ATC | ATC | CTC | TTT | TTG | GTA | GCA | GCA | GCT | ACA | GGT | GTC | CAC | TCC |
| CH12 | --- | --- | --- | --- | --- | --- | --- | --- | --- | --- | --- | --- | --- | --- | --- | --- | --- | --- | --- |
| germline V$_H$23 |  |  |  |  |  |  |  |  |  |  |  |  |  |  |  |  |  |  |  |

|  | 1<br>Q | V | Q | L | Q | Q | P | G | T | 10<br>E | L | V | K | P | G | A | S | V | K |
|---|---|---|---|---|---|---|---|---|---|---|---|---|---|---|---|---|---|---|---|
| SCH94.03 | CAG | GTC | CAA | CTG | CAG | CAG | CCT | GGG | ACT | GAA | CTG | GTG | AAG | CCT | GGG | GCT | TCA | GTG | AAG |
| CH12 | --- | --- | --- | --- | --- | --- | --- | --- | --- | --- | --- | --- | --- | --- | --- | --- | --- | --- | --- |
| germline V$_H$23 |  |  |  |  |  |  |  |  |  |  |  |  |  |  |  |  |  |  |  |

CDR1

|  | 20<br>L | S | C | K | A | S | G | Y | T | 30<br>F | T | S | Y | W | M | H | W | V |
|---|---|---|---|---|---|---|---|---|---|---|---|---|---|---|---|---|---|---|
| SCH94.03 | CTG | TCC | TGC | AAG | GCT | TCT | GGC | TAC | ACC | TTC | ACC | AGC | TAC | TGG | ATG | CAC | TGG | GTG |
| CH12 | --- | --- | --- | --- | --- | --- | --- | --- | --- | --- | --- | --- | --- | --- | --- | --- | --- | --- |
| germline V$_H$23 |  |  |  |  |  |  |  |  |  |  |  |  |  |  |  |  |  |  |

CDR2

|  | K | Q | R | 40<br>P | G | Q | G | L | E | W | I | G | 50<br>N | I | N | 52A<br>P | S | N | G |
|---|---|---|---|---|---|---|---|---|---|---|---|---|---|---|---|---|---|---|---|
| SCH94.03 | AAG | CAG | AGG | CCT | GGA | CAA | GGC | CTT | GAG | TGG | ATT | GGA | AAT | ATT | AAT | CCT | AGC | AAT | GGT |
| CH12 | --- | --- | --- | --- | --- | --- | --- | --- | --- | --- | --- | --- | --- | --- | --- | --- | --- | --- | --- |
| germline V$_H$23 |  |  |  |  |  |  |  |  |  |  |  |  |  |  |  |  |  |  |  |

FIG. 11B

CDR2

|  |  |  |  |  |  |  | 60 |  |  |  |  |  |  | 70 |  |  |  |
|---|---|---|---|---|---|---|---|---|---|---|---|---|---|---|---|---|---|
|  | G | T | N | Y | N | E | K | F | K | S | K | A | T | L | T | V | D | K | S |
| SCH94.03 | GGT | ACT | AAC | TAC | AAT | GAG | AAG | TTC | AAG | AGC | AAG | GCC | ACA | CTG | ACT | GTA | GAC | AAA | TCC |
| CH12 | --- | --- | --- | --- | --- | --- | --- | --- | --- | --- | --- | --- | --- | --- | --- | --- | --- | --- | --- |
| germline V_H23 | --- | --- | --- | --- | --- | --- | --- | --- | --- | --- | --- | --- | --- | --- | --- | --- | --- | --- | --- |

|  |  |  | 80 |  |  |  |  | 82A | 82B | 82C |  |  |  |  |
|---|---|---|---|---|---|---|---|---|---|---|---|---|---|---|
|  | S | S | T | A | Y | M | Q | L | S | S | L | T | S | E |
| SCH94.03 | TCC | AGC | ACA | GCC | TAC | ATG | CAG | CTC | AGC | AGC | CTG | ACA | TCT | GAG |
| CH12 | --- | --- | --- | --- | --- | --- | --- | --- | --- | --- | --- | --- | --- | --- |
| germline V_H23 | --- | --- | --- | --- | --- | --- | --- | --- | --- | --- | --- | --- | --- | --- |

CDR3

|  |  |  | 90 |  |  |  |  | N region |  |  | D region |  |  | 100 | 100A | 100B | N region |  |
|---|---|---|---|---|---|---|---|---|---|---|---|---|---|---|---|---|---|---|
|  | D | S | A | V | Y | Y | C | A | R | R | A | P | Y | Y | G | S | R |  |  |
| SCH94.03 | GAC | TCT | GCG | GTC | TAT | TAT | TGT | GCA | AGA | CGG | GCC | CC..T | TAC | TAC | GGT | AGT | AGG | ... | G |
| CH12 | --- | --- | --- | --- | --- | --- | --- | --- | --- | ... | . | D | --- | --- | --- | --- | S | W |  |
| germline V_H23 | --- | --- | --- | --- | --- | --- | --- | --- | --- |  |  | GA- |  |  |  |  |  |  |  |
| J_H2 |  |  |  |  |  |  |  |  |  |  |  |  |  |  |  |  | --C | TGG | GGG |

FIG. 11C

```
                          CDR3          |        J region
                     100C 100D
                       N   F   D   Y   W   G
SCH94.03         ... AAC TTT GAC TAC TGG GGC
CH12                   Y   Y
germline V_H23   TAC T--  ---  ---  ---  ---  ---
         J_H2             T--  ---  ---  ---  ---
```

```
                                    110                          |    Cμ
                 Q   G   T   T   L   T   V   S   S   E   S   Q
SCH94.03        CAA GGC ACC ACT CTC ACA GTC TCC TCA GAG AGT CAG
CH12            ---  ---  ---  ---  ---  ---  ---  ---  ---  ---  ---  ---
germline J_H2   ---  ---  ---  ---  ---  ---  ---  ---  ---
```

FIG. 11D

Leader region

```
                      -19                                                   -9
                       M   M   S   S   A   Q   F   L   G   L   L   L   C   F   Q   G
SCH94.03              ATG ATG TCC TCT GCT CAG TTC CTT GGT CTC CTG TTG CTC TGT TTT CAA GGT
CH12                  --- --- --- --- --- --- --- --- --- --- --- --- --- --- --- ---
germline Vκ10
```

Leader region

```
                                  1                                            10
                       T   R   C   D   I   Q   M   T   Q   T   T   S   S   L   S   A   S   L
SCH94.03              ACC AGA TGT GAT ATC CAG ATG ACA CAG ACT ACA TCC TCC CTG TCT GCC TCT CTG
CH12                  --- --- --- --- --- --- --- --- --- --- --- --- --- --- --- --- --- ---
germline Vκ10
```

CDR1

```
                                              20                               30
                       G   D   R   V   T   I   S   C   R   A   S   Q   D   I   S   N   Y   L   N
SCH94.03              GGA GAC AGA GTC ACC ATC AGT TGC AGG GCA AGT CAG GAC ATT AGC AAT TAT TTA AAC
CH12                  --- --- --- --- --- --- --- --- --- --- --- --- --- --- --- --- --- --- ---
germline Vκ10
```

FIG.11E

|  | W | Y | Q | Q | K | P | D | G | T | V | K | L | L | I | Y | Y | T | S |
|---|---|---|---|---|---|---|---|---|---|---|---|---|---|---|---|---|---|---|
|  |  |  |  |  | 40 |  |  |  |  |  |  |  |  |  | 50 |  |  |  |
|  |  |  |  |  |  |  |  |  |  |  |  |  |  |  |  |  | CDR2 |  |
| SCH94.03 | TGG | TAT | CAG | CAG | AAA | CCA | GAT | GGA | ACT | GTT | AAA | CTC | CTG | ATC | TAC | TAC | ACA | TCA |
| CH12 | --- | --- | --- | --- | --- | --- | --- | --- | --- | --- | --- | --- | --- | --- | --- | --- | --- | --- |
| germline Vκ10 | --- | --- | --- | --- | --- | --- | --- | --- | --- | --- | --- | --- | --- | --- | --- | --- | --- | --- |

|  | R | L | H | S | G | V | P | S | R | F | S | G | S | G | S | G | T | D |
|---|---|---|---|---|---|---|---|---|---|---|---|---|---|---|---|---|---|---|
|  |  |  |  |  |  |  |  | 60 |  |  |  |  |  |  |  |  |  | 70 |
|  | CDR2 |  |  |  |  |  |  |  |  |  |  |  |  |  |  |  |  |  |
| SCH94.03 | AGA | TTA | CAC | TCA | GGA | GTC | CCA | TCA | AGG | TTC | AGT | GGC | AGT | GGG | TCT | GGA | ACA | GAT |
| CH12 | --- | --- | --- | --- | --- | --- | --- | --- | --- | --- | --- | --- | --- | --- | --- | --- | --- | --- |
| germline Vκ10 | --- | --- | --- | --- | --- | --- | --- | --- | --- | --- | --- | --- | --- | --- | --- | --- | --- | --- |

|  | Y | S | L | T | I | S | N | L | E | Q | E | D | I | A | T | Y | F | C |
|---|---|---|---|---|---|---|---|---|---|---|---|---|---|---|---|---|---|---|
|  |  |  |  |  |  |  |  |  | 80 |  |  |  |  |  |  |  |  |  |
| SCH94.03 | TAT | TCT | CTC | ACC | ATT | AGC | AAC | CTG | GAG | CAA | GAA | GAT | ATT | GCC | ACT | TAC | TTT | TGC |
| CH12 | --- | --- | --- | --- | --- | --- | --- | --- | --- | --- | --- | --- | --- | --- | --- | --- | --- | --- |
| germline Vκ10 | --- | --- | --- | --- | --- | --- | --- | --- | --- | --- | --- | --- | --- | --- | --- | --- | --- | --- |

FIG. 11F

```
                              CDR3                                    J region
            90                                                  100
            Q   Q   G   N   T   L   P   W   T   F   G   G
SCH94.03    CAA CAG GGT AAT ACG CTT CCG TGG ACG TTC GGT GGA
                                        P
CH12        --- --- --- --- --- --- --- -T CC- --- --- ---
germline Vκ10 --- --- --- --- --- --- --T --- --- --- --- ---
Jκ1
```

```
                J region                                              Cκ
                                                           110
            G   T   K   L   E   I   K   R   A   D   A
SCH94.03    GGC ACC AAG CTG GAA ATC AAA CGG GCT GAT GCT
CH12        --- --- --- --- --- --- --- --- --- --- --T
germline Vκ10 --- --- --- --- --- --- --- --- --- --- ---
Jκ1         --- --- --- --- --- --- --- --- --- --- --T
```

MONOCLONAL ANTIBODIES WHICH PROMOTE CENTRAL NERVOUS SYSTEM REMYELINATION

GOVERNMENT SUPPORT

The invention described herein was supported in whole or in part by the National Institutes of Health, Grant No. NS-24180 and the National Multiple Sclerosis Society Grant No. RG-1878-B-2. The United States Government has certain rights in the invention.

BACKGROUND

Multiple sclerosis (MS) is a chronic, frequently progressive, inflammatory central nervous system (CNS) disease characterized pathologically by primary demyelination, usually without initial axonal injury. The etiology and pathogenesis of MS are unknown. Several immunological features of MS, and its moderate association with certain major histocompatibility complex alleles, has prompted the speculation that MS is an immune-mediated disease (Hafler, D. A. and Weiner, H. L., *Immunol. Today*, 10:104–107 (1989); Compston, D. A. S., "Genetic susceptibility to multiple sclerosis," In: *McAlpine's Mutiple Sclerosis* (Matthews, B. ed), pp 301–319, London: Churchil Livingstone (1991); Olsson, T., *Curr. Opin. Neurol. Neurosurg,*, 5:195–202 (1992)).

An autoimmune hypothesis is supported by the experimental autoimmune (allergic) encephalomyelitis (EAE) model, where injection of certain myelin components into genetically susceptible animals leads to T cell-mediated CNS demyelination (Kabat, E. A. et al., *J. Exp. Med.*, 85:117–129 (1947); Lublin, F. D., *Spinger Semin. Immunopathol.*, 8:197–208 (1985)). However, specific autoantigens and pathogenic myelin-reactive T cells have not been definitively identified in the CNS of MS patients, nor is MS associated with other autoimmune diseases. An alternative hypothesis, based upon epidemiological data (Martyn, C., "The epidemiology of multiple sclerosis. In: *McAlpine's Multiple Sclerosis*, (Matthews, B. ed), pp 3–40, London: Churchill Livingstone (1991) is that an environmental factor, perhaps an unidentified virus, precipitates an inflammatory response in the CNS, which leads to either direct or indirect ("bystander") myelin destruction, potentially with an induced autoimmune component (Lampert, P. W., *Am. J. Path.* 91:176–208 (1978)). This hypothesis is supported by evidence that several naturally occurring viral infections, both in humans (Rice, G. P. A., *Curr. Opin. Neurol. Neurosurg.*, 5:188–194 (1992)) and animals (Dal Canto, M. C. and Rabinowitz, S. G., *Ann. Neurol.*, 11:109–127 (1982)), can cause demyelination. One commonly utilized experimental viral model is induced by Theiler's murine encephalomyelitis virus (TMEV) (Dal Canto, M. C., and Lipton, H. L., *Am. J. Path.*, 88:497–500 (1977)).

The limited efficacy of current therapies for MS and other demyelinating diseases (Goodkin, D. E. et al., *Clev. Clin. J. Med.*, 59:63–74 (1992)), has stimulated interest in novel therapies to ameliorate these diseases (Martin, R., et al., *Ann. Rev. Immunol.*, 10:153–187 (1992); Steinman, L., *Adv. Immunol.*, 49:357–379 (1992); Weiner, H. L., et al., science 259:1321–1324 (1993)). However, due to the apparently complex etiopathogenesis of these diseases, potentially involving both environmental and autoimmune factors, the need still exists for an effective treatment of these demyelinating disorders.

SUMMARY OF THE INVENTION

The present invention relates to the promotion, or stimulation, of remyelination of central nervous system axons in a mammal. Specifically, the present invention relates to methods of stimulating the remyelination of central nervous system (CNS) axons using a monoclonal antibody obtained from a mammal-immunized with spinal cord homogenate (SCH) from a normal mammal (i.e., uninfected with any demyelinating disease). This monoclonal (mAb) is referred to herein as SCH94.03, and the hybridoma producing this monoclonal antibody has been deposited on Apr. 28, 1994, under the terms of the Budapest Treaty, with the American Type Culture Collection (ATCC) and given ATCC Accession No. CRL 11627. As demonstrated herein, treatment of a mammal afflicted with a demyelinating disease using the mAb, SCH94.03, resulted in an increase in CNS remyelination compared to mice treated with control mAb.

The present invention also relates to methods of treating demyelinating diseases in mammals, such as multiple sclerosis in humans, and viral diseases of the central nervous system of humans and domestic animals, such as post-infectious encephalomyelitis, or prophyiactly inhibiting the initiation or progression of demyelination in these disease states, using the SCH94.03 monoclonal antibody. This invention further relates to in vitro methods of producing, and stimulating the proliferation of, glial cells, such as oligodendrocytes, and the use of these glial cells to treat demyelinating diseases.

BRIEF DESCRIPTION OF THE FIGURES

FIG. 3(A) Light micrograph of spinal cord section from a chronically infected SJL/J mouse treated with SCH94.03 showing CNS remyelination. FIG. 3(B) Light micrograph of spinal cord section from a chronically infected SJL/J mouse treated with a control IgM showing extensive demyelination, and the relative absence of remyelination. Inflammatory cells, including macrophages with ingested myelin debris are indicated by arrows. The asterisk indicates a representative naked axon. FIG. 3(C) Light micrograph of spinal cord section with normal myelin. FIG. 3(D) Electron micrograph of spinal cord section from an animal treated with SCH94.03 showing multiple axons with abnormally thin myelin sheaths relative to axon diameter. The star in the upper right-hand corner indicates an axon with normal myelin sheath thickness. Arrowheads point to astrocytic processes, which are intimately associated with remyelinated axons. Scale bars represent 13 μm in A–C, and 2 μm in D.

FIGS. 8A–8C shows the results of SCH94.03 (FIG. 8A) and control IgMs (FIG. 8B and 8C) binding to protein antigens as determined by ELISA.

FIGS. 10A–10C show the results of SCH94.03 (FIG. 10A) and control IgMs (FIG. 10B and 10C) binding to chemical haptens as determined by ELISA, FIGS. 11A14 11F show the alignment of the immunoglobulin light and heavy chain variable region sequences of SCH94.03 and control IgM, CH12, and germline Ig gene segments (SEQ ID NOS: 1–11).

DETAILED DESCRIPTION OF THE INVENTION

Figure 1:
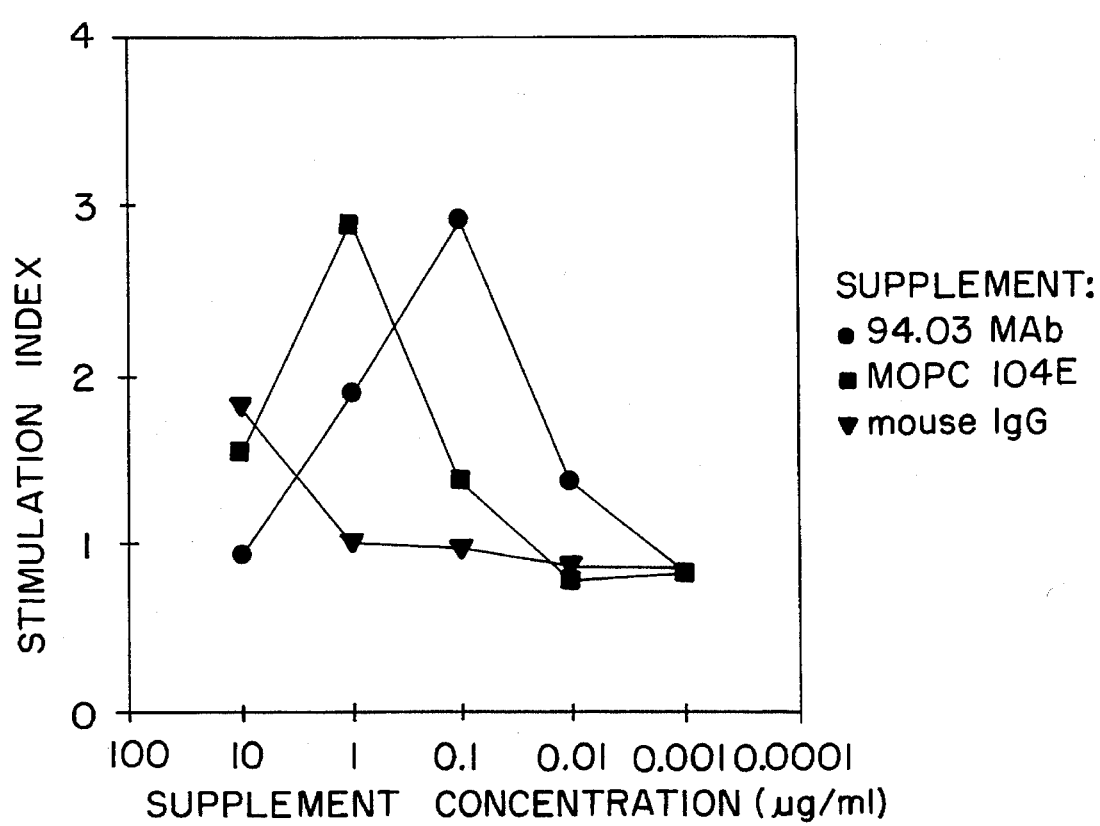
FIG. 1 is a graph depicting the dose-response characteristics of antibody-mediated proliferation of cells in mixed rat brain culture.

The present invention relates to the promotion, or stimulation, of remyelination of central nervous system axons in a mammal. Specifically, the present invention relates to methods of stimulating the remyelination of central nervous system (CNS) axons using a monoclonal antibody obtained from a mammal immunized with spinal cord homogenate from a normal mammal (i.e., uninfected with any demyelinating disease). The antigen reactivity of the monoclonal antibody, an IgM monoclonal antibody referred to herein as SCH94.03 (also referred to herein as SCH94.32) has been characterized as described in the present invention using several biochemical and molecular assays, including immunohistochemistry, immunocytochemistry, Western blotting, solid-phase enzyme-linked immunosorbant assays (ELISA), and Ig variable region sequencing. The hybridoma producing monoclonal antibody SCH94.03 has been deposited on Apr. 28, 1994, under the terms of the Budapest Treaty, with the American Type Culture collection (ATCC) 12301 Parklawn Drive, Rockville, Md. 20852-1776, and has been given ATCC Accession No. CRL 11627. All restrictions upon the availability of the deposit material will be irrevocably removed upon granting of the patent.

The present invention also relates to methods of treating demyelinating diseases in mammals, such as multiple sclerosis in humans, and viral diseases of the central nervous system of humans and domestic animals, such as post-infectious encephalomyelitis, using the SCH94.03 monoclonal antibody. Methods of prophylactic treatment using the mAb to inhibit the initiation or progression of demyelinating diseases are also encompassed by this invention.

Selection of SCH mAbs to promote CNS remyelination

A panel of monoclonal antibodies (mAbs) derived from splenocytes of uninfected SJL/J mice injected with SCH was constructed as described in detail in Example 1. After the initial fusion and cloning, 2 of the 95 wells with viable Ig-secreting hybridomas contained mAb with significant binding to SCH as demonstrated by ELISA. Hybridoma cells from these two wells, called the 79 and 94 series, were subcloned by limiting dilution and screened again for binding to SCH by ELISA. For the 79 series hybridomas, 14 out of 49 clones were positive by SCH ELISA, while for the 94 series, 17 out of 32 were positive for binding to SCH. Based upon the ELISA data, two 79 series hybridomas (SCH79.08 and SCH79.27), both of which also reacted with myelin basic protein (MBP) by ELISA, and three 94 series hybridomas (SCH94.03, SCH94.11, and SCH94.32), none of which reacted with MBP, were chosen for ascites production and in vivo transfer experiments.

MAbs Promote Proliferation of Glial Cells

As described in Example 2, the mAbs were tested for their ability to promote proliferation of glial cells in vitro. As shown in Table 1, rat optic nerve cells grown in the presence of mAb 94.02 or 79.27 incorporated more [3H]thymidine than controls grown in media alone or with an isotype-matched control mAb. Data is shown from one of five experiments which showed a similar result.

TABLE 1

Monoclonal Antibodies to Spinal Cord Homogenate Promote Incorporation of [³H]Thymidine in Cultured Optic Nerve Glial Cells

| Additive in Medium | μg/ml | CPM Mean + SE | Stimulation Index Isotype Control | P | Stimulation Index PBS | P |
|---|---|---|---|---|---|---|
| mAb 94.32 | 3 | 3,642 ± 364 | 2.68 | <0.01 | 2.17 | <0.01 |
| mAb 79.27 | 3 | 2,326 ± 182 | 1.71 | <0.01 | 1.38 | <0.05 |
| Isotype Control | 3 | 1,359 ± 82 | 1.00 | — | 0.81 | — |
| PBS | — | 1,680 ± 203 | 1.23 | — | 1.00 | — |
| mAb 94.32 | 10 | 4,663 ± 114 | 2.78 | <0.002 | 1.90 | <0.01 |
| mAb 79.27 | 10 | 2,711 ± 176 | 1.62 | NS | 1.11 | NS |
| Isotype Control | 10 | 1,678 ± 213 | 1.00 | — | 0.68 | — |
| PBS | — | 2,451 ± 946 | 1.46 | — | 1.00 | — |
| mAb 94.32 | 30 | 3,855 ± 639 | 4.01 | <0.03 | 2.44 | <0.002 |
| mAb 79.27 | 30 | 4,037 ± 371 | 4.20 | <0.04 | 2.56 | <0.003 |
| Isotype Control | 30 | 962 ± 191 | 1.00 | — | 0.61 | — |
| PBS | — | 1,578 ± 231 | 1.64 | — | 1.00 | — |

The dose-response characterisitcs of antibody-mediated proliferation were then examined. As shown in FIG. 1, maximal stimulation with 94.03 was seen at 100 ng/ml. Control myeloma IgMs MOPC 104E and TEPC 183 (data not shown) also stimulated the mixed rat brain cultures to proliferate. However, the maximal effect was seen at a 10-fold higher concentration than that seen with the mAbs.

Figure 2:
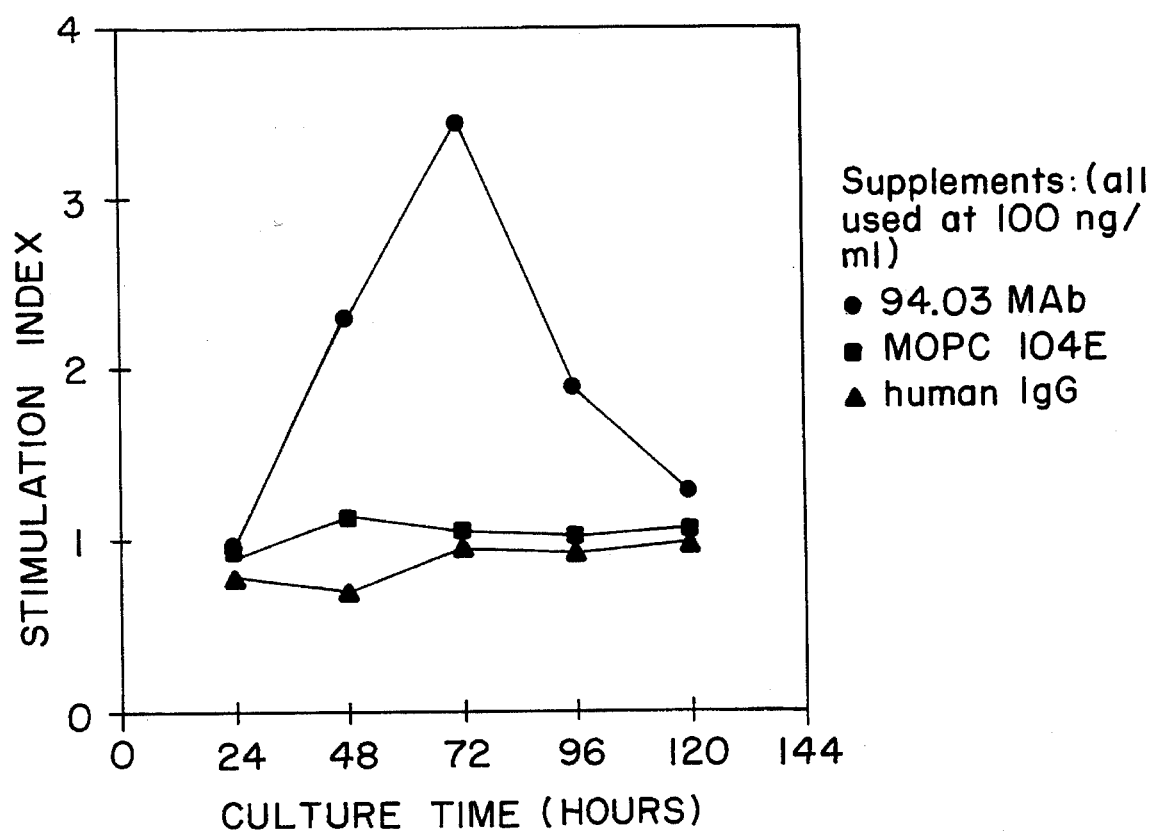
FIG. 2 is a graph depicting the temporal profile of antibody-mediated proliferation of cells in mixed rat brain culture.

The temporal profile of antibody-mediated proliferation was also examined as shown in FIG. 2. On day 8, after culture initiation, 100 ng/ml antibody was added to the cultures (time 0). Cells were harvested at 24 hour intervals; [$^3$H]thymidine was present for the final 24 hours of culture to measure the total proliferation during the interval. The maximal stimulation with 94.03 was seen at 72 hours after antibody addition. Similar results were obtained with 94.32. None of the isotype control antibodies showed any significant proliferation throughout the 120 hours of culture. These data demonstrates that both mAbs 94.32 and 94.03 induce proliferation of glial cells of mixed rat brain culture. This proliferation is maximal at an antibody concentration of 100 ng/ml and a culture period of 72 hours after antibody addition.

CNS Remyelination Promoted by mAbs SCH94.03 and SCH94.32

As described in Example 3, SJL/J mice chronically infected with TMEV were treated with a total mAb dose of 0.5 mg iv or 5.0 mg ip divided into twice weekly doses for 4–5 weeks. CNS remyelination was measured by a quantitative morphological assessment on ten spinal cord cross-sections from each mouse. The criterion for CNS remyelination was abnormally thin myelin sheaths relative to axonal diameter. The data are composite of six experiments and are presented as the mean±SEM, where n indicates the number of mice. Statistical comparisons for remyelination data were made with the cumulative values from both IgM and buffer only controls using a modified rank sum test. The number of demyelinated lesions and the area of demyelination were not significantly different between treatment groups assessed by a one-way ANOVA. For control IgMs, we used myelomas MOPC 104E and ABPC 22 (both from Sigma), and TB5-1, an anti-mycobacteria mAb.

SJL/J mice chronically infected with TMEV and treated with either mAb SCH94.03 or SCH94.32 showed significantly greater CNS remyelination than animals treated with either isotype-matched control mAb or buffer only (Table 2).

highly significant ($p<0.005$; Table 2). In a chronic progressive disease like TMEV infection, the extent of CNS repair is a direct function of the extent of CNS damage. Both the number and area of CNS lesions were not different between treatment groups, indicating similar disease severity (Table 2). When CNS remyelination was expressed as the percentage of lesion area showing remyelination, approximately one-third of the cumulative demyelinated lesion area showed CNS remyelination in mice treated with either mAb SCH94.03 or SCH94.32 (Table 2).

Morphology of CNS Remyelination

Figure 3A:
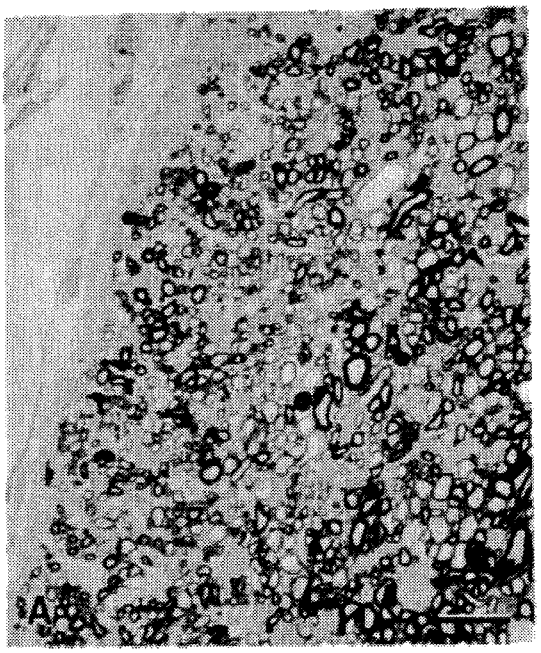
FIG. 3A–3D shows light and electron micrographs of CNS remyelination promoted by mAb SCH94.03.
Figure 3B:
Figure 3C:
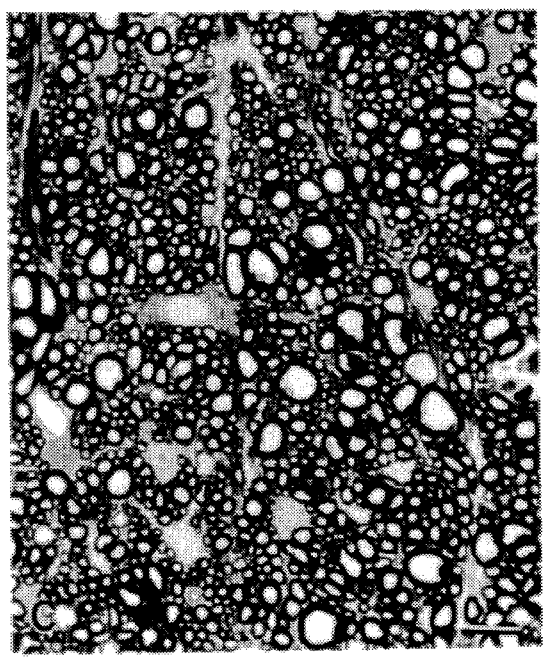
Figure 3D:
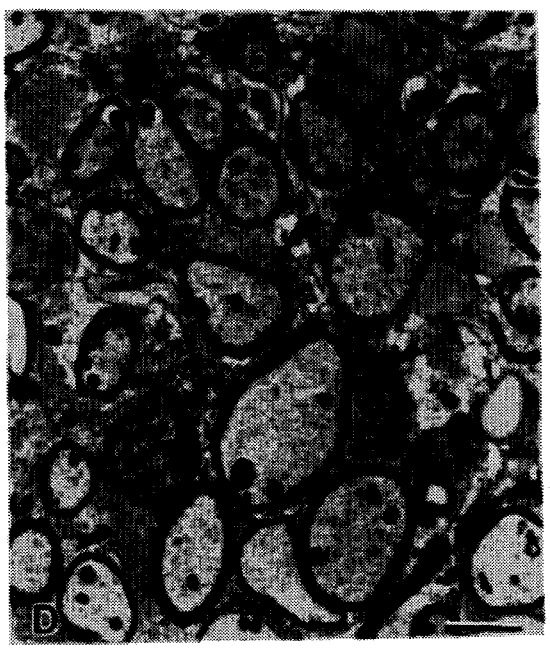

CNS remyelination was readily identified morphologically both by light and electron microscopy (FIG. 3A–3D). FIG. 3A shows a remyelinated lesion from an animal treated with SCH94.03. The majority of axons in the lesion show morphologic evidence of repair, with abnormally thin myelin sheaths relative to axonal diameter (Ludwin, S. K. "Remyelination in the central nervous system of the mouse," In: THE PATHOLOGY OF THE MYELINATED AXON (Adachi M, Hirano A, Aronson SM eds), pp 49–79, Tokyo: Igaku-Shoin Ltd. (1985); Ludwin, S. K., *Adv. Neurol.*, 47:215–254 (1988)). For comparison, FIG. 3B shows a demyelinated lesion, with minimal remyelination, whereas FIG. 3C is an area of normal myelin, with thickly myelinated axons. Within remyelinated lesions (FIG. 3A), there were 15.3±1.0 (mean±SEM) myelinated axons per 100 m$^2$, compared to only 1.1±0.2 myelinated axons per 100 μm$^2$ in demyelinated lesions (FIG. 3B). FIG. 3C shows a light micrograph of spinal cord section with normal myelin. By electron microscopy, CNS remyelination was especially evident (FIG. 3D). Almost every axon in the field has evidence of new myelin formation, although the degree of remyelination (i.e. myelin thickness) is variable between individual axons, suggesting different stages of the repair process. The ratio of myelin thickness to axonal diameter was 0.08±0.01 (mean±SEM; n=25 axons) for remyelinated axons compared to 0.21±0.01 (n=34 axons) for normally myelinated axons.

Correlation Between Clinical Disease and Morphological Remyelination

The correlation of morphological remyelination with clinical signs of disease improvement was assessed as described in Example 3. At each treatment injection, mice

TABLE 2

Monoclonal antibodies SCH94.03 and SCH94.32 promote CNS remyelination

| Treatment | n | Number Remyelination Lesions | Area of Remyel (mm$^2$) | p-value | Number of Demyelination Lesions | Area of Lesion (mm$^2$) | Area Remyel inatio n/Area Lesion (%) |
|---|---|---|---|---|---|---|---|
| SCH94.03 | 12 | 12.8 ± 2.6 | 0.35 ± 0.09 | <0.0025 | 25.8 ± 2.6 | 1.09 ± 0.19 | 28.9 ± 3.8 |
| SCH94.32 | 12 | 12.3 ± 2.3 | 0.42 ± 0.11 | <0.0001 | 24.9 P ± 2.8 | 1.46 ± 0.21 | 26.7 ± 4.2 |
| IgM control | 13 | 6.7 ± 1.2 | 0.11 ± 0.02 | — | 29.9 ± 2.0 | 1.70 ± 0.28 | 7.7 ± 1.8 |
| Buffer only | 11 | 5.1 ± 1.1 | 0.06 ± 0.01 | — | 27.7 ± 2.7 | 1.11 ± 0.29 | 6.5 ± 1.2 |

Figure 4:
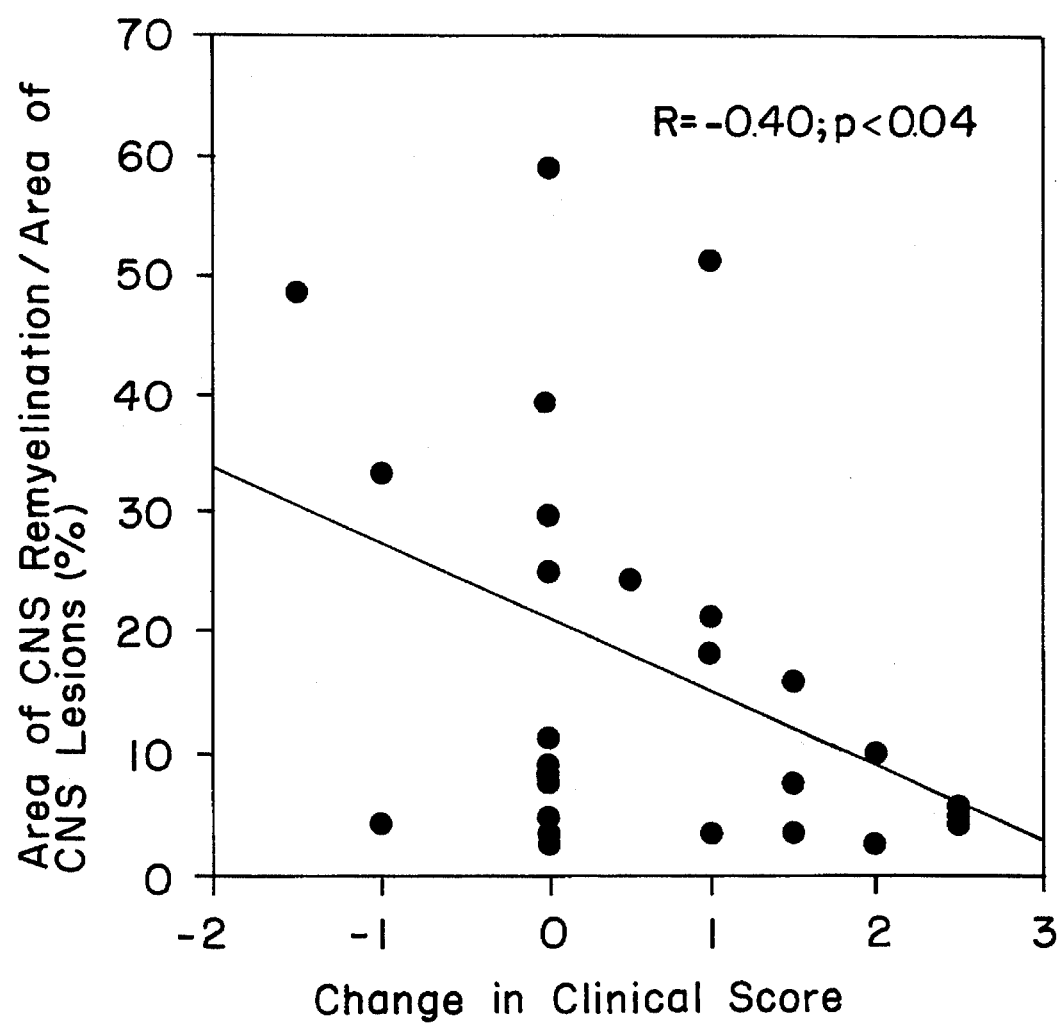
FIG. 4 is a graph depicting the correlation between the change in clinical disease and morphological remyelination.

Remyelination was seen with either iv or ip injections. SCH94.03- or SCH94.32-treated animals had approximately 2–3-fold more remyelinated lesions, and a 3–4-fold larger total area of CNS remyelination than control animals. When a cumulative statistical comparison was made using these two parameters of therapeutic effectiveness, the CNS remyelination induced by mAbs SCH94.03 and SCH94.32 was were assessed clinically as described in Example 3. The change in clinical score was correlated with the percentage of lesion area showing remyelination (FIG. 4). Morphological remyelination is represented as the percentage of lesion area showing CNS remyelination. A change in clinical score of 0 represent stable disease over the treatment period (4–5 weeks), whereas a positive change indicates worsening of clinical disease, and a negative change indicates improvement. Data represent individual animals from all treatment groups. A positive change in clinical score indicates worsening of disease. Using data from all treatment groups, the change in clinical score showed a moderate but significant negative correlation ($R=-0.40$; $p<0.04$) with the percentage of lesion area showing remyelination. Although few animals actually improved clinically ($\Delta$ clinical score<0), animals with an increase in disease severity ($\Delta$ clinical score>0) tended to have less morphological remyelination, while animals that remained stable clinically ($\Delta$ clinical score=0) showed the most remyelination. A similar negative correlation was obtained when the other quantitative measures of remyelination were used (the number of remyelinated lesions and the area of remyelination) as shown in Table 2. These data demonstrate that remyelination quantitated by morphology is associated with slowing of clinical disease progression.

Titration of mAb SCH94.03 Dose and CNS Remyelination

Figure 5:
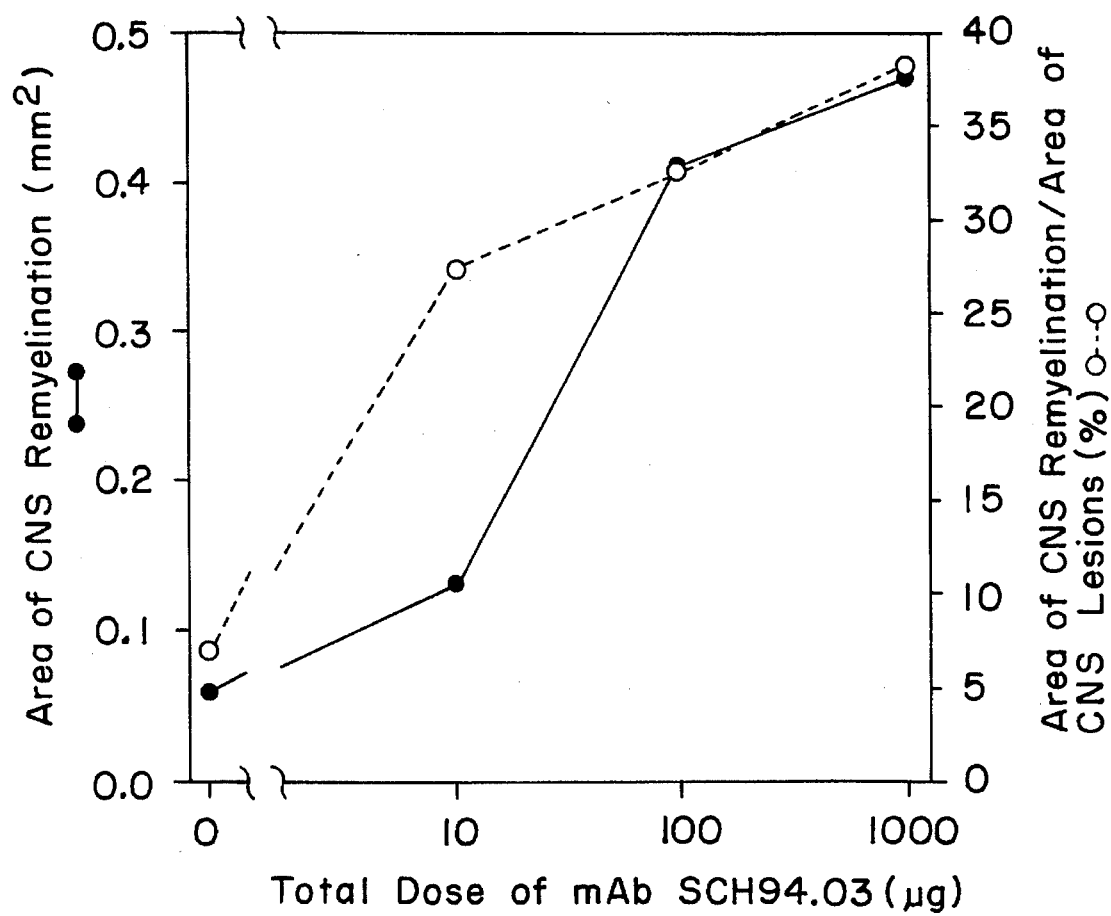
FIG. 5 is a graph depicting the dose-response relationship between treatment with mAb SCH94.03 and CNS remyelination. Area of CNS remyelination (●) and percentage of lesion area with remyelination (o) in animals treated with various doses of mAb SCH94.03.

For the initial treatment experiments, a total mAb dose of 25 mg/kg for iv injections and 250 mg/kg for ip injection was empirically chosen. To assess the dose-response characteristics, and to determine the minimal amount of mAb needed to promote remyelination, chronically-infected mice were treated with various ip doses of SCH94.03. Both the number of remyelinated lesions (data not shown) and the total area of remyelination (FIG. 5) increased significantly with larger doses of SCH94.03. Remyelination was quantitated as described for Table 2. Data are the mean values of 4–5 animals per mAb dose, with the final cumulative dose indicated on the graph. SEM averaged 35% of the mean. There was no statistical difference assessed by one-way ANOVA in the number of demyelinated lesions or the area of demyelination between treatment groups, indicating similar extent of disease in all animals. The number of demyelinated lesions and area of lesions were 33.2±7.5 and 1.25±0.43 for the 1000 µg group, 31.8±8 and 1.11±0.31 for the 100 µg group, 23.8±3.4 and 0.54±0.14 for the 10 µg group, and 29.0±6.5 and 0.74±0.20 for the buffer only group (represented as the 0 dose point on the graph). Animals treated with 100 µg control IgM (MOPC 104E) had remyelination scores similar to control animals treated with buffer only. The positive correlation between the dose of mAb SCH94.03 and CNS remyelination was especially striking when the severity of CNS disease was taken into account. When CNS repair was expressed as the percentage of lesion area showing remyelination, mice treated with a total dose of 1000, 100, or 10 µg of SCH94.03 had 6-, 5-, and 4-fold more remyelination than control animals, respectively (FIG. 5). Mice given as little as 10 µg of SCH94.03 ip (0.5 mg/kg) showed evidence of enhanced CNS remyelination. These data indicated that mAb SCH94.03 and CNS remyelination had a positive dose-response relationship, and that very small quantities of mAb were needed to promote myelin repair.

Antigen Specificity of SCH94.03 and SCH94.32

Figure 6:
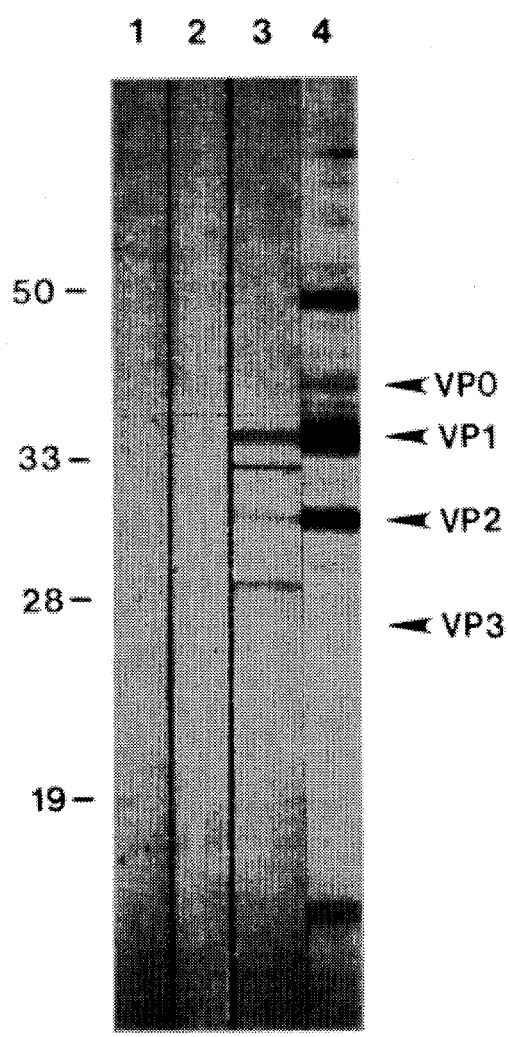
FIG. 6 shows a Western blot of TMEV proteins. Lysates from infected L2 fibroblast cells were separated by SDS-PAGE, transferred to nitrocellulose, and blotted with SCH94.03 (lane 1), SCH94.32 (lane 2), serum from susceptible mice chronically infected with TMEV (lane 3), and polyclonal rabbit anti-TMEV IgG (lane 4). Molecular weights are indicated on the left in kilodaltons (kDa). The position and identification of the major TMEV capsid proteins are indicated on the right.

Although mAbs SCH94.03 and SCH94.32 were generated from splenocytes of uninfected mice, and screened against SCH from uninfected mice, it was directly assessed whether either mAb could react with TMEV capsid proteins or inhibit viral infectivity in vitro. By Western blotting (FIG. 6), SCH94.03 and SCH94.32 did not react with any TMEV proteins recognized by either serum from chronically infected mice or polyclonal IgG from rabbits injected with purified TMEV (Rodriguez, M., et al., *Ann. Neurol.*, 13:426–433 (1983)). Western blot of lysates from control mock infected L2 cells showed single bands with the serum from chronically infected animals and the polyclonal rabbit anti-TMEV IgG at 32 and 43 kDa, respectively, but no reactivity with SCH94.03 or SCH94.32.

In addition, no significant inhibition of TMEV infectivity in vitro with up to 5 µg/ml of either SCH94.03 or SCH94.32, was observed under assay conditions where 50% neutralization was observed with a 1:34,000 dilution of serum from chronically infected animals. These results indicated that the therapeutic effect of SCH94.03 and SCH94.32 was not due to direct inhibition of the virus.

Figure 7A:
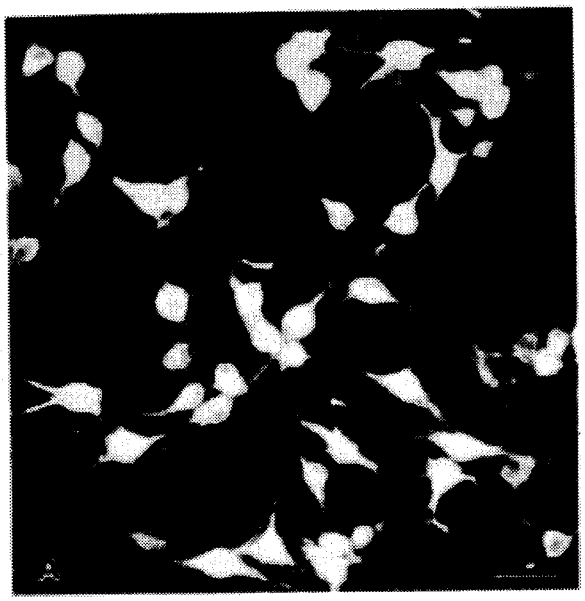
FIGS. 7A–7D show the immunostaining of cultured glial cells (FIGS. 7A and 7B) and frozen CNS tissue sections (FIGS. 7C and 7D) with mAb SCH94.03. Scale bars represent 15 μm.
Figure 7B:

To initially characterize the antigens recognized by mAbs SCH94.03 and SCH94.32, various cell lines derived from glial (rat C6, mouse G26-20, human U373MG and U87MG), neural (human neuroblastoma), fibroblast (mouse L and 3T3), epithelial (human SCC-9 carcinoma), and lymphocytic (mouse CTLL2) origin were stained. Both mAbs stained internal antigens of all cell lines tested, which indicated that certain antigens recognized by these mAbs were not restricted to unique cell types in vitro. Based on the hypothesis that the therapeutic effect of SCH94.03 and SCH94.32 was due to a CNS-specific interaction, the immunostaining of cultured cells by SCH94.03 and SCH94.32 using the rat glial cell line 5.5B8 was further investigated. This immortalized glial cell line has phenotypic characteristics of both ac and astrocytes, with expression of MBP and 2',3'-cyclic nucleotide 3'-phosphodiesterase (CNP), and low but detectable expression of glial fibrillary acidic protein (GFAP) and the lipids or proteins recognized by the mAbs A2B5 and 04 (Bozyczko, D. et al., *Ann. NY Acad. Sci.*, 605:350–353 (1990)). SCH94.03 and SCH94.32 recognized both a surface and cytoplasmic determinant on 5.5B8 cells. The surface staining was most prominent on small cells which lay on top of a layer of flat, morphologically differentiated cells (FIG. 7A). Surface staining was confirmed by flow cytometry on live cells. When the cell membrane was permeabilized by dehydration or brief treatment with a non-ionic detergent to expose internal antigens, the staining pattern was altered considerably (FIG. 7B). The cytoplasmic staining was filamentous, with a dense perinuclear network that extended out into the cell processes. This pattern closely resembled the staining pattern of the intermediate filament cytoskeletal protein vimentin. These data indicated that SCH94.03 and SCH94.32 recognized antigens that were not restricted to cells derived from the nervous system, but that they did recognize both surface and cytoplasmic determinants on glial cells.

Figure 7C:
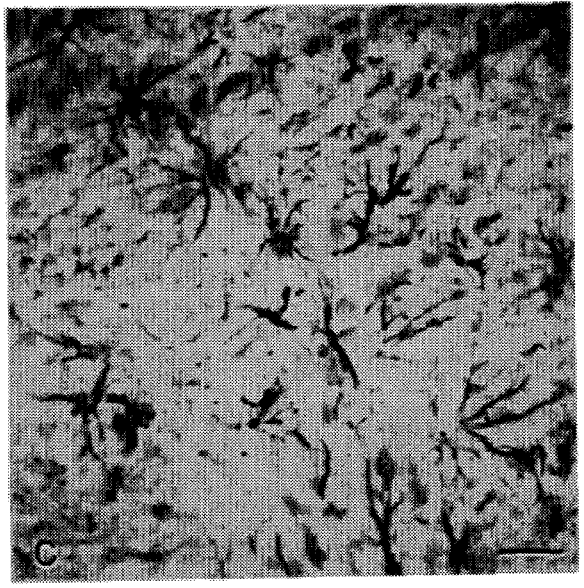
Figure 7D:
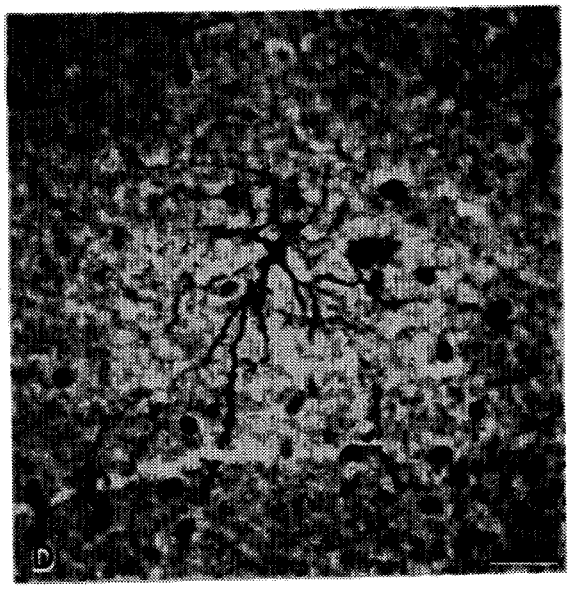

Immunohistochemical staining of frozen mouse, rat, and human tissue confirmed that SCH94.03 and SCH94.32 were not CNS-specific mAbs, but rather showed multi-organ reactivity. Both mAbs immunostained all major organs examined, including the brain, spinal cord, optic nerve, heart, liver, kidney, stomach, and small intestine and skeletal muscle. However, not all cells within an organ stained, suggesting in situ cytological specificity. Within the CNS, SCH94.03 and SCH94.32 stained predominantly blood vessels, ependymal cells, and stellate-shaped cells with the morphological features of glial cells, which were enriched in neonatal cerebellar, periventricular, and brain stem white matter (FIG. 7C), and both neonatal and adult optic nerve. Similar glial cells positive for SCH94.03 and SCH94.32 were found in autopsied human brain tissue, especially at the gray-white matter junction (FIG. 7D). Identical immunostaining results were obtained with mAb SCH94.32.

Immunostaining with a control IgM (MOPC 104E) was negative for all samples and tissue structures which immunostained with SCH94.03 and SCH94.32.

The identification and characterization of an entire family of autoantibodies, referred to as "natural" or "physiological" autoantibodies, has influenced traditional views of autoimmunity and self-reactivity. The natural autoantibodies that have been studied extensively are typically IgMs, although other isotypes have been identified, are reactive toward a wide range of antigens, including cytoskeletal proteins, surface proteins, nucleic acids, phospholipids, bacterial antigens such as lipopolysaccharideS, and various chemical haptens (reviewed by Avrameas and Ternynck, *Mol. Immunol.*, 30:1133–1142 (1993)). Natural autoantibodies share extensive idiotypic cross-reactivity or "connectivity", which includes expression of similar idiotypes, some of which are expressed by pathogenic autoantibodies, as well as reactivity toward common idiotypes expressed on other antibodies. Molecular analysis has shown that natural autoantibodies are typically encoded by unmutated germline immunoglobulin (Ig) genes, with few if any somatic mutations, and therefore represent a substantial fraction of the Ig repertoire, especially in neonatal animals which have not had extensive exogenous antigen exposure.

The function of natural autoantibodies remains enigmatic. Several hypotheses have been proposed based upon their biochemical and molecular characteristics. These include: (1) clearance of senescent or damage tissue, (2) providing a first line of immunological defense in the lag period between pathogen exposure and an Ag-specific immune response, (3) masking autoantigeus from a potentially pathogenic autoimmune response, (4) immunomodulation, including shaping of the neonatal immune repertoire via an idiotypic network, and (5) participation in the positive selection of B cells in the bone marrow, similar to the process proposed for T cells in the thymus.

The hypothesis that antibodies SCH94.03 and SCH94.32 were natural autoantibodies was tested. To characterize the antigen reactivities of SCH94.03 and SCH94.32, several biochemical and molecular assays, including immunohistochemistry and immunocytochemistry, Western blotting, solid-phase enzyme-linked immunosorbant assays (ELISA), and Ig variable region sequencing, were used. As described below, for all biochemical assays, SCH94.03 and SCH94.32 were indistinguishable. In addition, SCH94.03 and SCH94.32 had identical Ig variable region sequences, which confirmed that they were the same mAb.

A potential mechanism whereby SCH94.03 could stimulate remyelination in the central nervous system would be to stimulate the proliferation and/or differentiation of cells involved in myelinogenesis, primarily oligodendrocytes or their immature precursors. Thus, it was tested whether SCH94.03 stained the surface of various cells. Using immortalized cells, it was determined that SCH94.03 stained two glial cells lines, 5.5B8 (FIG. 7A) and 20.2E11, but did not stain the surface of several other glial cells lines (10.IA3, 20.2A40, C6, G26-20), a neuroblastoma cell line (B104), two fibroblast lines (L2, Cos-1), or two myoblastomas (G8, L6). Similar results were obtained with cells isolated from animal tissues and grown in culture. SCH94.03 stained the surface of oligodendrocytes, but not astrocytes, microglia, Schwann cells, myoblasts, or fibroblasts.

The reactivity of SCH94.03 with proteins from glial and lymphoid cell lines, and tissue lysates from brain, liver, and intestine by Western blotting was also assessed. SCH94.03 reacted with multiple bands from all cells and tissues examined, with prominent reactivity toward bands at 50, 95, 120, and >200 kDa. The exact identity of these protein bands has not been determined.

Figure 8A:
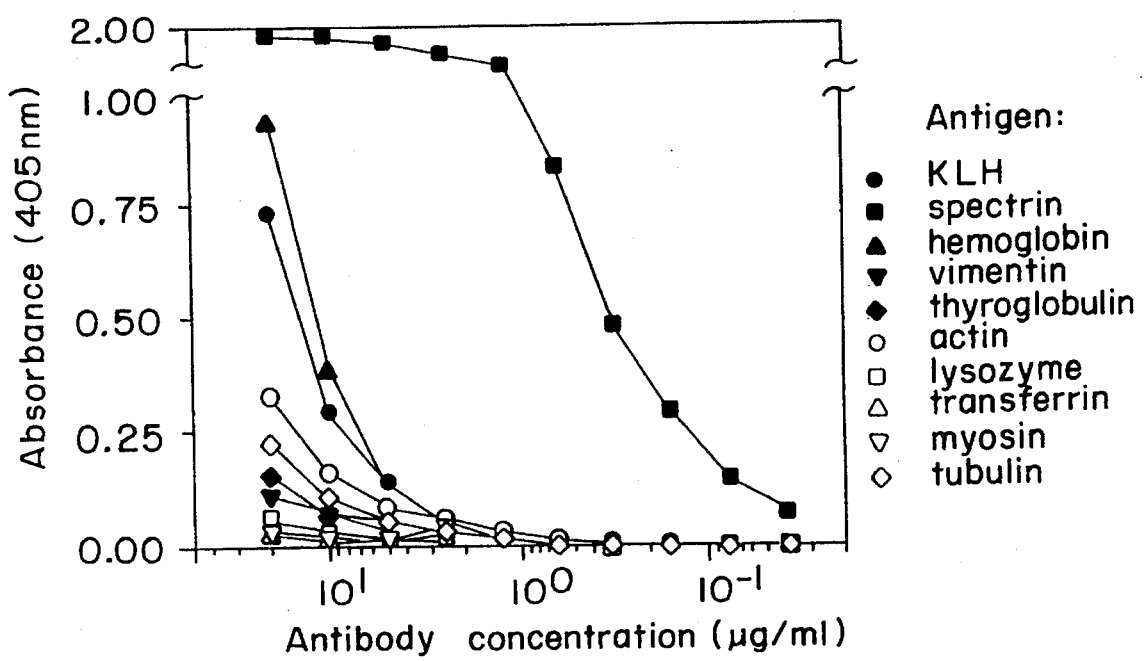
Figure 8B:
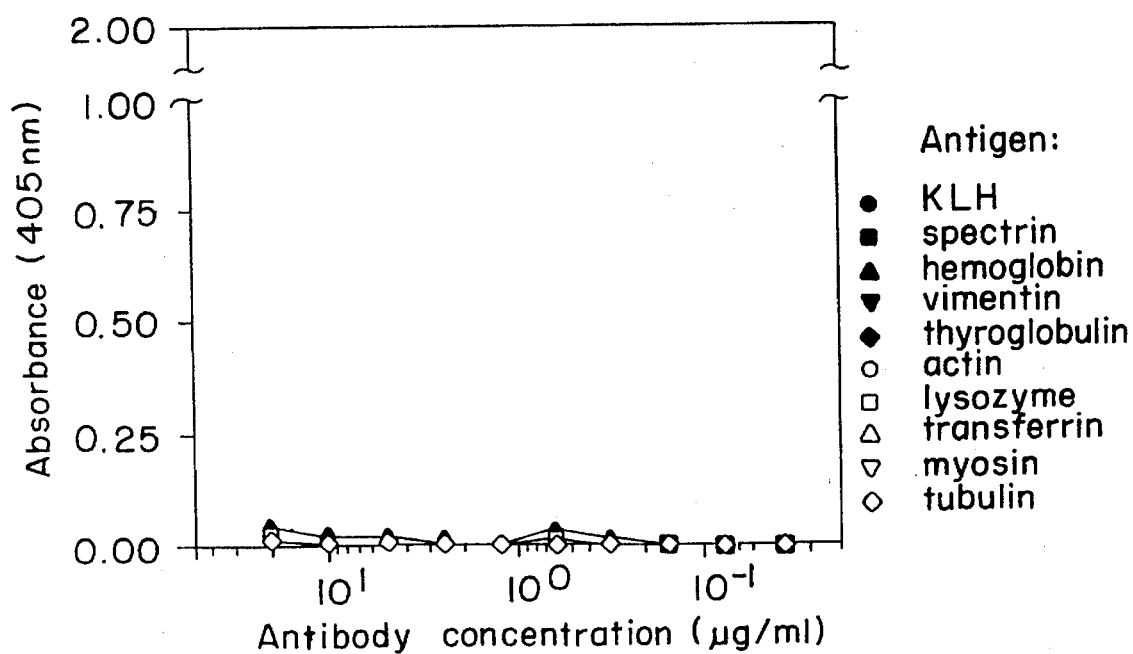

The reactivity of SCH94.03 with several purified protein self-antigens by solid-phase ELISA was determined. (FIG. 8A–8C). SCH94.03 showed strong reactivity toward the RBC antigen spectrin, but also showed consistent reactivity toward hemoglobin, actin, tubulin, and vimentin, and thyroglobulin, although to a lesser qualitative degree than toward spectrin. No reactivity was observed with myosin, transferrin, albumin, lysozyme, or myelin basic protein under our assay conditions. Six other monoclonal or myeloma IgM controls XXMEN-OE5 (FIG. 8B), A2B5, MOPC104E, TEPC183, 01, and CH12 (FIG. 8C), were also tested, and no reactivity with any of the antigens tested was observed.

Figure 9:
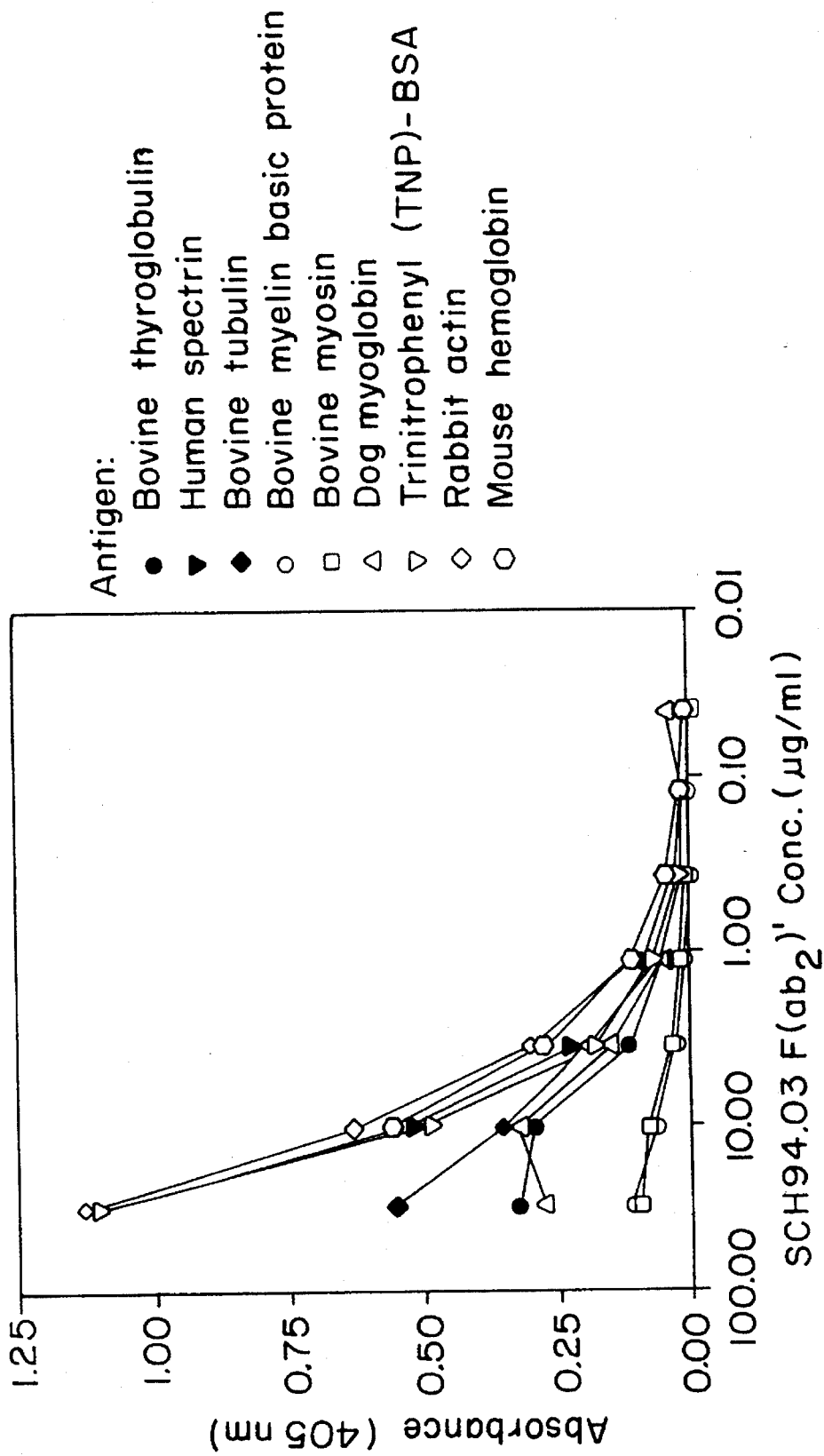
FIG. 9 shows the results of SCH94.03 F(ab2)' binding to protein antigens as determined by ELISA.

To confirm the monoclonality of SCH94.03, 18 subclones of SCH94.03 (9 each from SCH94.03 and SCH94.32 parents) were tested for polyreactivity by solid-phase ELISA. All 18 subclones showed identical reactivity patterns with the panel of protein antigens as the parent SCH94.03. To further support the conclusion that the polyreactivity of SCH94.03 was via its Fab region, we generated $F(ab)_2'$ fragments and assessed their reactivity with the protein antigens by ELISA (FIG. 9). SCH94.03 $F(ab)_2'$ fragments showed similar polyreactivity as the whole IgM molecule.

Figure 10A:
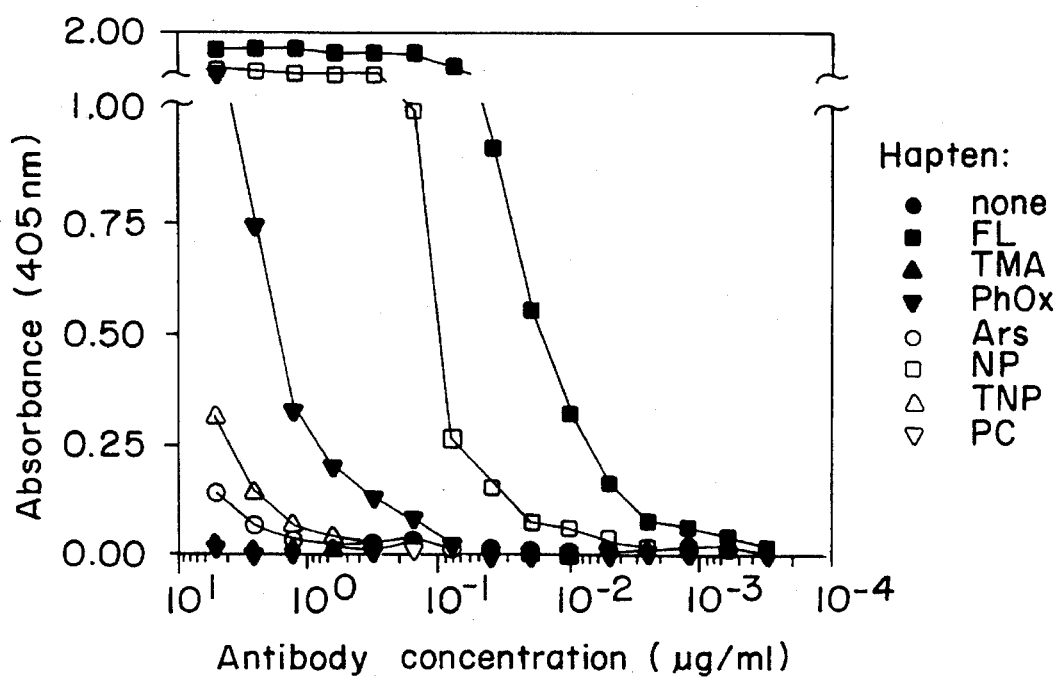
Figure 10B:
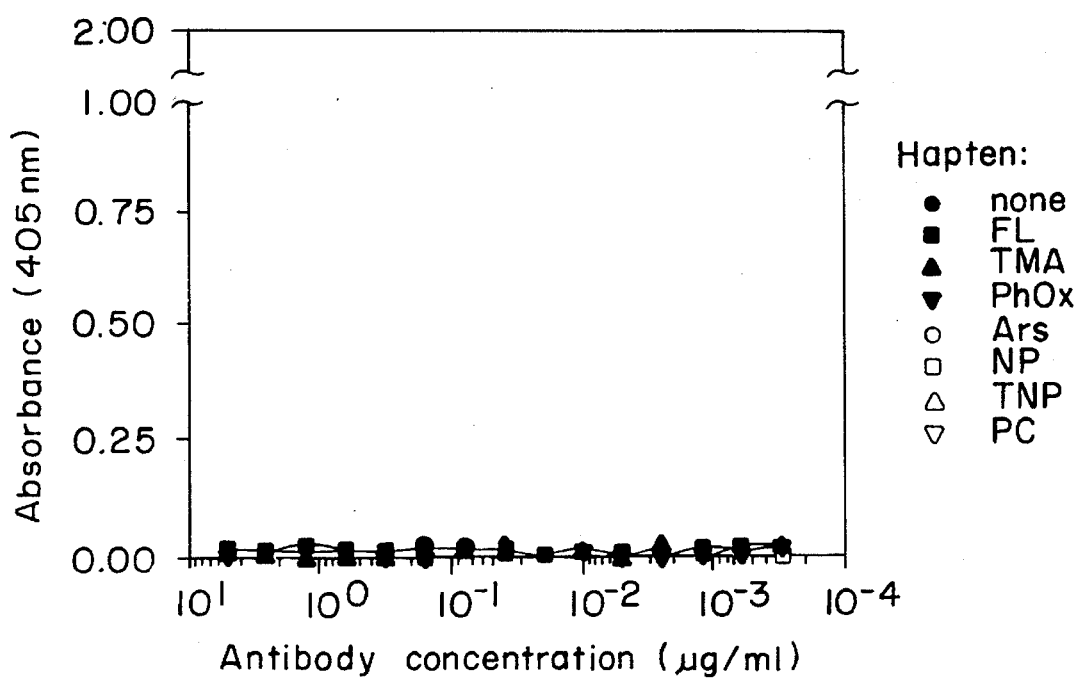

A panel of chemical haptens coupled to bovine serum albumin (BSA) was constructed and used to assess SCH94.03 reactivity by solid-phase ELISA (FIG. 10A–10C). SCH94.03 showed strong reactivity toward fluorescein (FL) and 4-hydroxy-3-nitrophenyl acetic acid (NP), moderate reactivity toward phenyloxazolone (PhOx), and weak reactivity toward 2, 4, 6-trinitrophenyl (TNP) and p-azophenylarsonic acid (Ars). No reactivity with p-azophenyltrimethylammonium (TMA), p-azophenylphosphorylcholine (PC), or the carrier protein BSA was detected. Control IgMs (FIG. 10B and 10C) showed no significant binding to any of the haptens tested, with the exceptions of CH12 reactivity with TMA, which has been previously reported, and A2B5 reactivity with NP.

It was further investigated whether the Ig light (L) (SEQ ID NOS: 1 and 2 and heavy (H) (SEQ ID NOS: 6 and 7) chains of SCH94.03 were encoded by germline Ig genes (FIG. 11). The light chain variable ($V_L$) and joining ($J_L$) region nucleotide sequences from SCH94.03 (SEQ ID NOS: 1 and 2) had 99.4% identity with the previously published sequences of the germline $V_{K10}$ (SEQ ID NO. 4) and $J_{K1}$ (SEQ ID NO. 5) genes, with only two silent changes at the 3' end of both the $V_L$ and $J_L$ regions. The SCH94.03 $V_H$ (SEQ ID NOS: 6 and 7) region nucleotide sequence was identical to the previously published germline $V_H 23$ (SEQ ID NO: 10) sequence, the $J_H$ region sequence differed from the published germline $J_H 2$ (SEQ ID NO: 11) sequence by one nucleotide, at the 5' end of the J region, and the diversity (D) region contained 15 contiguous nucleotides derived from the germline DFL16.1 gene. There were 8 nucleotides in the V-D junction, and 1 in the D-J junction, which did not correspond to any known germline V or D region genes, and probably represent noncoded (N) nucleotides inserted by the enzyme terminal deoxynucleotide transferase during V-D-J recombination. The only changes from the germline genes in the heavy chain of SCH94.03 occurred at either the V-D or D-J junction, and therefore could represent either N nucleotides or the result of imprecise joining, rather than somatic mutations. In addition, both the light and heavy chain variable regions of SCH94.03 showed extensive sequence similarity with the IgM produced by the B-cell lymphoma CH12 (SEQ ID NOS: 3, 8 and 9) (FIG. 11).

SCH94.03 is a Natural Autoantibody

These preliminary antigen reactivity results suggest that SCH94.03 is a natural autoantibody. Although this conclusion does not readily present a mechanism as to how SCH94.03 stimulates remyelination in the central nervous system, it does suggest an important physiological function of natural autoantibodies. Autoantibodies that are produced either during normal physiology, or in response to tissue damage and the subsequent release of previously sequestered antigens, might actively participate to promote repair in the damaged tissue. In line with previously proposed functions of natural autoantibodies, this active participation might be to facilitate removal of damaged tissue, mask autoantigens thereby preventing a vigorous pathogenic autoimmune response, modulate the immune response which actually resulted in the tissue destruction, thereby allowing normal endogenous tissue repair to occur, or directly stimulate cells involved in the repair process.

Thus, as a result of the work described herein, it is now demonstrated that an autoantibody generated and screened for its autoantigen-binding capability, also promotes CNS remyelination. Mice chronically infected with TMEV and treated either iv or ip with IgM mAbs from hybridomas SCH94.03 or SCH94.32 had significantly more CNS repair than control animals, measured by a detailed quantitative morphological assessment of CNS remyelination. Moreover, preliminary data suggest that the autoantibody, SCH94.03 is also effective in promoting remyelination in mammals afflicted with experimental autoimmune encephalomyelitis (EAE). Thus, it is reasonable to predict that autoantibodies, such as SCH94.03, play a critical role in stopping an immune-mediated process of demyelination in CNS diseases.

Two potential mechanisms can be proposed by which Abs promote remyelination. First, Abs might inhibit some pathogenic component of the disease process, such as virus activity, an immune response which directly induces demyelination, or an immune response which prevents remyelination. If the disease outcome is based upon a balance between tissue destruction and repair, inhibition of pathogenic components would allow a physiological repair response to predominate. Experimental and clinical evidence support this hypothesis. Spontaneous CNS remyelination is seen in MS patients and several experimental models of CNS demyelination as well as described herein, demonstrating spontaneous remyelination in control mice. This indicates that remyelination is a normal physiological response to myelin damage. In addition, treatment of mice chronically infected with TMEV with various immunosuppressive regiments promotes remyelination, but does not decrease demyelination, indicating that there is an immunological component which inhibits remyelination. (Rodriguez, M. and Lindsley, M. D., Neurology, 42:348–357 (1992)). Preliminary immunological function studies have indicated that animals treated with SCH94.03 had similar numbers of B and T (both CD4+ and CD8+) cells in their spleens compared to control animals, had similar in vitro splenocyte proliferative responses to mitogens and antigens, and mounted comparable Ab responses to both T cell-dependent and T cell-independent antigens.

The second hypothesis is that certain Abs can actively stimulate CNS remyelination, perhaps via stimulation of oligodendrocyte proliferation and/or differentiation in vivo, as has been demonstrated in vitro (Diaz, M. et al., Brain Res., 154:231–239 (1978); Raine, C. S., et al., Lab. Invest., 38:397–403 (1979); Lehrer, G. M. et al., Brain Res., 172:557–560 (1979); Bansal, R. et al., J. Neurosci. Res., 21:260–267 (1988); Benjamins, J. A. and Dyer, C. A., Ann. NY Acad. Sci., 605:90–100 (1990); Dyer, C. A., Mol. Neurobiol., 7:1–22 (1993)). MAb SCH94.03 may directly stimulate precursor glial cells which are known to be present at the edges of both human and experimental CNS lesions which show active remyelination. Alternatively, SCH94.03 may work indirectly, via activation of astrocytes or other accessory cells, which could release factors important for the survival or proliferation of cells in the oligodendroglial lineage. The formation of Ab-antigen complexes in situ with tissue components released upon myelin destruction may also participate in Ab-mediated CNS remyelination. Although SCH94.03 is not CNS-specific, the recognition of both surface and cytoplasmic antigens on glial cells by the mAb supports an active mechanism hypothesis. In contrast to the immunomodulatory hypothesis, which would not necessarily require that Abs have direct access to the CNS, the hypothesis that Abs actively stimulate CNS remyelination implies the prerequisite of direct access to the CNS. This is contrary to the view of the selective permeability of the blood-brain barrier, especially toward large molecules such as pentameric IgM. However, during chronic inflammatory conditions such as TMEV infection or MS, peripheral leukocytes migrate into the CNS, indicating an alteration in the blood-brain barrier permeability. Therefore, large proteins such as serum Ig might also enter, via either passive diffusion through "open" endothelium, or perhaps via an unidentified active transport mechanism.

Treatment of Demyelinating Diseases

The results of the experiments described herein have practical applications to multiple sclerosis (MS), EAE, and other related central nervous system demyelinating disorders. Rare examples of spontaneous CNS-type remyelination ("shadow plaques") are found in MS and occasional peripheral nervous system (PNS)-type remyelination is found in demyelinated spinal cord plaques near the root entry zone. Oligodendrocytes are infrequent at the center of the chronic plaques in MS but they appear to proliferate at the periphery of plaques, where they are associated with abortive remyelination. The process of remyelination may correlate with the spontaneous remission and improvements observed clinically in MS. These clinical observations indicate that new myelin formation is possible in MS. The remyelination that has been stimulated in mice with TMEV-induced demyelination by using a mAb may hold promise for therapeutic application in multiple sclerosis.

Of importance clinically is the question of whether morphologic regeneration of thin myelin sheaths contributes to functional recovery. Computer simulations indicate that new myelin formation even by inappropriately thin sheaths improves impulse conduction. Since the axon membrane of normally myelinated fibers is highly differentiated, it is necessary for sodium channels to be present at high density at the node of Ranvier to propagate saltatory conduction. Experimental evidence suggests that newly formed nodes do develop the required high sodium channel density as demonstrated by saxitoxin binding. Data to date suggest that remyelination even by inappropriately thin myelin improves conduction in a previously demyelinated axon. Therefore, any strategy to promote this morphologic phenomenon has the potential of producing functional recovery.

The data presented herein demonstrates, for the first time, that administration of a monoclonal antibody to a mammal is capable of stimulating remyelination of central nervous system axons in vivo. Specifically, treatment of chronically infected TMEV-infected mice with as little as 10 ug of SCH94.03 resulted in a 4- to 5-fold increase in the total area of CNS myelination compared to mice treated with a control mAb.

Thus, as a result of the experiments described herein, the method of the present invention can be used to treat mammals, including humans and domestic animals, afflicted with demyelinating disorders, and to stimulate remyelination of the CNS axons. As described herein, an effective amount of the monoclonal antibody can be administered by intravenous (iv) or intraperitoneal (ip) injection. An effective amount of the antibody can vary depending on the size of the mammal being treated, the severity of the disease, the route of administration, and the course of treatment. For example, each dose of mAb administered can range from approximately 0.5 mg/kg to approximately 400 mg/kg, with the preferred range from approximately 0.5 mg/kg to approximately 250 mg/kg. It is important to note that a dose as low as 10 μg (0.5 mg/kg) was effective in promoting remyelination of CNS axons in mice. The dose of mAb will also depend on the route of administration. For example, an iv dose administered to mice was 0.5 mg/kg, and an ip dose was 5.0 mg/kg. The course of treatment includes the frequency of administration of the mAb (e.g, daily, weekly, or bi-weekly) and the duration of the treatment (e.g, four weeks to four months). Thus, for example, a larger amount of mAb can be given daily for four to five weeks, as opposed to a smaller amount of mAb given for four months.

The effectiveness of the amount of the monoclonal antibody being administered can be assessed using any number of clinical criteria, for example, as described in Example 3, including overall appearance of the mammal, the activity of the mammal and the extent of paralysis of the mammal. The effectiveness of the amount of monoclonal antibody necessary to induce remyelination in humans can also be assessed in a double blinded controlled trial. Patients with fixed neurological deficits from demyelinating disease can be treated with monoclonal antibody or controls. Improvement in isometric muscle strength as detected by quantitative biomechanics muscle testing could be used as the primary therapeutic end-point.

An effective amount of the monoclonal antibody can be combined with, or diluted with, an appropriate pharmaceutically acceptable carrier, such as a physiological buffer, or saline solution. Additionally, the monoclonal antibody may be genetically altered, e.g. "humanized" by the substitution of human antibody nucleotide sequences in nonvariable regions of the murine mAb to reduce immunogenicity.

In addition to in vivo methods of promoting remyelination, ex vivo methods of stimulating remyelination in CNS axons are also encompassed by the present invention. For example, the monoclonal antibody may be used in vitro to stimulate the proliferation and/or differentiation of glial cells, such as oligodendrocytes, as described in Example 2. These exogenous glial cells can then be introduced into the CNS of mammals using known techniques. Remyelination of CNS axons would be increased by increasing the number of endogenous glial cells present (glial cells, such as oligodendrocytes play a critical role in the production of myelin).

In vitro methods of producing glial cells, or stimulating the proliferation of glial cells from mixed culture (e.g., rat optic nerve cell, or rat brain cell cultures) are also encompassed by this invention. For example, cells obtained from rat optic nerve, or rat brain, containing glial cells, are cultured as a mixed culture under conditions sufficient to promote growth of the cells. An effective amount of mAb capable of promoting remyelination of CNS axons, such as SCH94.03, is then added to the mixed culture of cells and maintained under conditions sufficient for growth and proliferation of cells. The mAb stimulates the proliferation of glial cells in the mixed culture. Thus the proliferation of glial cells cultured in the presence of the mAb is increased, relative to the proliferation of glial cells grown in the absence of the mAb.

The invention will be further and more specifically illustrated by the following Examples, which are not intended to be limiting in any way.

EXAMPLE 1

Monoclonal Antibody Production, Screening and Purification

Animals

Spleens of two SJL/J mice (Jackson Laboratories, Bar Harbor, Me.) that had been injected twice with spinal cord homogenate (SCH) in incomplete Freund's adjuvant were used as the source of B cells for fusion and hybridoma production. Splenocytes were fused with NS-1 myeloma cells using polyethylene glycol, and viable cell fusions were selected with hypoxanthine-aminopterin-thymidine (HAT) media and cloned by limiting dilution as described (Katzmann, J. A. et al., *Proc. Nat. Acad. Sci. USA*, 78:162–166 (1981)).

ELISAs

Hybridoma supernatants from viable Ig-producing clones were screened for binding to SCH by an enzyme-linked immunosorbant assay (ELISA). The following antigens were used for screening mAbs: SCH—(10 μg) reconstituted in carbonate-bicarbonate buffer (pH 8.53), MBP—(1 μg) dissolved in PBS, GC (1 μg) dissolved in absolute alcohol, PLP (1 μg) dissolved in water. PLP was provided by Dr. W. Macklin (UCLA) who has published a solid phase immunoassay for PLP. For SCH, MBP or GC ELISA, Immuno II plates were coated with prepared antigen (100 μl/well) which was incubated overnight at 4° C. The following day wells were washed in PBS and blocked with PBS+1% serum for 1 hr at room temperature. Plates were washed again in PBS and serial dilutions of primary Ab diluted in PBS/0.1% BSA were added and incubated at room temperature for 2 hrs. Plates were washed in PBS/0.05% Tween and appropriate secondary Ab conjugated to alkaline phosphatase (1:1000 in PBS 0.1% BSA) was added. Plates were incubated at 37° C. for 2 hrs, washed in PBS 0.05% Tween, and the substrate (Sigma 104 Phosphatase Substrate Tablet in 5 ml diethanolamine buffer) was added for 30 min. The reaction was terminated with 50 μl of 1N NaOH. The plates were read on a Dynatech ELISA plate reader.

Ascites production

The hybridomas chosen for treatment experiments were injected into pristane-treated BALB/c mice for ascites production. Hylridomas were also grown in RPM1-1640 media supplemented with 10% fetal bovine serum for IgM production. IgM mAbs were purified by either ammonium sulfate precipitation and gel filtration on a Sephacryl S-400 HR (Sigma) column for the initial transfer experiments, or by affinity chromatography using goat anti-mouse IgM (μ-chain specific; Jackson Immunoresearch, West Grove, Pa.) coupled to Reacti-Gel 6× matrix (Pierce, Rockford, Ill.) for later transfer experiments.

EXAMPLE 2

In Vitro Testing of Monoclonal Antibodies Selection of mAbs that promote glial cell proliferation The ability of the mAbs to promote proliferation of glial cells in vitro was tested. Glial cells isolated from rat brain or optic nerves were seeded in Falcon Microtest II plates at a concentration of $2\times10^4$ cells per well in 0.1 ml of DME. Whole serum (SCH, IFA, MBP, GC, MBP/GC, PBS or PLP), purified Ig or mAb, was serially diluted and 0.1 ml aliquot was added to cells and assayed in triplicate. Three days later $^3$H-thymidine was added (1 µCi/ml) and cells were harvested after 17 hrs with an automated cell harvester (Mash II Harvester). To document identity of cells proliferating (i.e., , astrocytes, progenitor glial cells, macrophages), selected cultures after exposure to $^3$H-thymidine, were incubated with appropriate Ab specific for cell type followed by ABC immunoperoxidase technique. After reaction of Hanker-Yates reagent, the slides were immersed in Ilford K2 nuclear emulsions, exposed for 4 days at 4° C. and developed.

mAb 94.03 and 94.32 induce proliferation of mixed rat optic nerve brain cultures One- to two-day-old rats were killed with ether. Through careful dissection, optic nerves were removed from the optic nerve chiasm to the eye. Nerves were transferred to centrifuge tubes containing 2 mls of DMEM. An equal volume of 0.25% trypsin was added and incubated to 37° C. in a water bath for 45 min. 0.2 ml of FCS was added to terminate trypsinization. Nerves were passed through a sterile needle and syringe (gauge no. 21) and then centrifuged at 1400 rpm for 10 min. The cell count was adjusted to provide concentration of $5\times10^5$ cells/100 µl of media in 24-well trays in DMEM+0.5% FCS. After 12 to 16 hrs, appropriate antibodies or growth media were added as per experimental protocols.

Brains of 1–2 day old rats were removed and placed in Hank's Balanced Salt Solution with 10 mM HEPES buffer (HBSS/H), approximately 1–2 ml per brain. The brain stem, cerebellum, and midbrain was discarded whereas the forebrain was minced with a bent syringe. The tissue was further disrupted by repeated passage through a 10 ml pipet and transferred to a 50 ml conical tube. The tissue suspension was shaken on a rotary shaker (75 rpm) for 30 min at 37° C. Trypsin was added to a final concentration of 0.125% and the suspension was shaken for an additional 60 min. Trypsin digestion was stopped by adding FCS (10%). The cell suspension was passed sequentially through 120 and 54 µm Nytex, centrifuged, resuspended in serum-free medium with 10% FCS, and filtered again through 54 µm Nytex. Serum-free media was DMEM with 3.7 g/l sodium bicarbonate, 6.0 g/l glucose, 2 mM L-glutamine, 0.1 nM nonessential amino acids, 5 µg/ml insulin, 5 µg/ml transferrin, 5 ng/ml selenite, 100 U/ml penicillin and 100 µg/ml streptomycin. The cells were counted, plated onto uncoated tissue culture flasks or plates at $5\times10^4$ cells/cm$^2$ and cultured at 37° C. in 5% $CO_2$. The media was changed after 72 hrs, and every 48 hrs thereafter. On day 8 after culture initiation, the media was aspirated and replaced by SFM with various supplements (for example, antibody). For most experiments, the cells were grown for an additional 48 hrs before harvesting. Cells were pulsed with [$^3$H]thymidine (5 µCi/ml) for the final 1824 hrs of culture.

Western Blot Procedure

Antigens were denatured and solubilized by heating at 100° C. in sodium dodecyl sulfate (SDS) sample buffer. Samples were electrophoresed on stacking and separating gels containing 4.75% and 12.0% acrylamide at 200 volts. After electrophoresis, gels and nitrocellulose membranes were equilibrated for 30 min in transfer buffer (25 mM Tris, 192 mM glycine, 20% methanol, pH 8.1–8.3). All steps were done at room temperature. Gels were electroblotted for either 1 hr at 100 V or overnight at 30 V using the Bio-Rad Mini Trans-blot apparatus. The nitrocellulose membrane was cut into strips and washed, 3× TBS (100 mM NaCl, 50 mM TriG, pH 7.6) with 0.03% Tween 20. Nitrocellulose strips were blocked (TBS with 3% non-fat milk and 0.03% Tween 20) for 2–4 hrs, washed 3×, and incubated with primary Ab or antisera (diluted in blocking buffer) for 4 hrs or overnight. After primary Ab incubation, strips were washed 3×, incubated with either biotin- or alkaline phosphate-labelled secondary Ab (diluted in blocking buffer) for 2 hrs, washed 3×, and incubated with alkaline-phosphatase labeled-streptavidin (diluted in blocking buffer) for 2 hrs if the biotin system is used. Nitrocellulose strips were washed 4× (final wash in TBS without Tween 20) and incubated with substrate solution (0.165 mg/ml BCIP and 0.33 mg/ml NBT in 100 mM NaCl, 100 mM TriG, 5 mM MgG12, pH 9.5) until sufficient color developed (approximately 10–15 min). The reaction was stopped by adding PBS with 5 mM EDTA.

Cell lines or mixed brain cultures were lysed in 1× SDS reducing sample buffer (2.3% SDS, 10% 2-ME, 0.125M Tris, 20% glycerol) and heated to 85° C. for 15 min. Nucleic acids were sheared by repeated passage of lysate through 21–27-gauge needles. Lysate proteins were separated on a 12% acrylamide reducing gel, transferred to nitrocellulose membranes, and blotted with various antibodies as previously described.

EXAMPLE 3

Promotion of CNS Remyelination Using a Monoclonal Antibody

Virus

The DA strain of TMEV was obtained from Drs. J. Lehrich and B. Arnason after eight passages in BHK cells. The virus was passaged an additional four times at a multiplicity of infection of 0.1 plaque forming units (PFU) per cell. Cell-associated virus was released by freeze-thawing the cultures followed by sonication. The lysate was clarified by centrifugation and stored in aliquots at −70° C. All subsequent experiments will use passage 12 virus. This virus isolate causes white matter pathology without destruction of anterior horn cells.

In vitro TMEV neutralization assay

Viral plaque assays were done as previously described (Patick, A. K., et al., *J. Neuropath. Exp. Neurol.*, 50:523–537 (1991)). To assess neutralization, aliquots of TMEV (200 PFU/ml) were incubated with various concentrations of Ab for 1 hour at room temperature prior to plating onto confluent L2 cells. As a positive control, we used serum from susceptible mice chronically infected with TMEV. Under the assay conditions described above, a serum dilution of 1:34,000 gave 50% neutralization, which corresponded to an estimated 20 ng/ml of TMEV-specific Abs, assuming a total serum Ig concentration of 15 mg/ml, and a TMEV-specific fraction of 5%.

Demyelination protocol

Demyelination was induced in female SJL/J mice, ages four to six weeks, from the Jackson Laboratory, Bar Harbor, Me. Mice were inoculated intracerebrally with $2\times10^5$ plaque-forming units of DA virus in a volume of 10 µl. Mice infected chronically with TMEV (4 to 6 months following infection) were assigned randomly to groups of treatment.

Treatment protocol and clinical disease assessment

Chronically infected mice were given either intraperitoneal (ip) or intravenous (iv) injections of mAb twice weekly for 4–5 weeks. At each treatment injection, mice were assessed clinically by three criteria: appearance, activity, and paralysis. A score for each criterion was given ranging from 0 (no disease) to 3 (severe disease). For appearance, 1 indicated minimal change in coat, 2 indicated a moderate change (scruffy appearance), and 3 indicated a severe change (incontinence and stained coat). For activity, 1 indicated decreased spontaneous movements (minimal ataxia), 2 indicated moderate slowing (minimal spontaneous movements), and 3 indicated severe slowing (no spontaneous movement). For paralysis, 0.5 indicated a spastic extremity, 1 indicated a paralyzed extremity, 1.5 indicated two or more spastic extremities, 2 indicated two paralyzed extremities (unable to walk), 2.5 indicated no righting response, and 3 indicated three or four paralyzed extremities (moribund). The total score for each mouse was the cumulative total from each criterion (maximum of 9). As the clinical score was an ordinal, but not a cardinal scale, the change in clinical score to assess clinical disease was used. The clinical assessment data were not disclosed until after the morphological assessment of remyelination was completed.

Light and electron micrograph preparation and assessment of remyelination

Preparation of light and electron microscopy sections and morphological assessment of remyelination were done. Briefly, treated mice were anesthetized with pentobarbital (0.2 mg ip), exsanguinated by cardiac puncture, and killed by intracardiac perfusion with Trump's fixative (100 mM phosphate buffer, pH 7.2, with 4% formaldehyde and 1.5% glutaraldehyde). The entire spinal cord was removed carefully from the spinal canal, and sectioned into 1 mm transverse blocks. Every third block was post-fixed in 1% osmium tetroxide and embedded in Araldite (Polysciences, Warrington, Pa.). One micron sections from each block were cut and stained with p-phenylenediamine. On each section, remyelination was quantitated using a Zeiss interactive digital analysis system (ZIDAS) and camera lucida attached to a Zeiss photomicroscope (Carl Zeiss Inc., Thornwood, N.Y.). Abnormally thin myelin sheaths relative to axonal diameter was used as the criterion for CNS remyelination. Ten spinal cord sections from each mouse were examined; this corresponded to 8–9 mm² of white matter examined per mouse. To avoid bias, slides were coded and quantitation was done without knowledge of the treatment groups.

Myelin thickness and axonal diameter measurements and quantitation of myelinated axons Electron micrographs of normal and remyelinated axons from plastic-embedded spinal cord sections were imaged with a Hamamatsu video camera, digitized, and analyzed using an IBAS 2000 Image Analysis System (Kontron, Munich, Germany). The axonal cross-sectional area with and without the myelin sheath was measured, and equivalent circle calculations were used to determine the axonal diameter and myelin sheath thickness. For myelinated axon quantitation, the number of myelinated axons in lesions from plastic-embedded spinal cord sections were counted using the analysis system described above attached to an Axiophot microscope (Carl Zeiss, Inc.). 17 remyelinated and 15 demyelinated lesions in spinal cord sections from animals treated with mAb SCH94.03, control IgM, or buffer only were analyzed. This corresponded to 0.6 mm² of remyelinated area and 0.8 mm² of demyelinated area. The criterion for selection of a lesion as demyelinated was the presence of substantial demyelination with minimal repair, whereas remyelinated lesions were chosen based upon the presence of almost complete remyelination throughout the lesion.

Immunostaining

Rat 5.5B8 glial cells were grown on poly-D/L-lysine-coated chamber slides in Dulbecco's modified Eagle's medium (DMEM) supplemented with 1.5 g/L D-glucose, 30 nM $SeO_2$, 15 nM triiodothyronine, 10 ng/ml biotin, 100 µM $ZnCl_2$, 50 µg/ml gentamicin, and 10% fetal bovine serum. All staining steps were done at room temperature. For surface staining, slides were briefly rinsed with PBS, and cells were lightly fixed with 1% formaldehyde in PBS for 10 min to prevent cell detachment during subsequent staining steps. For cytoplasmic staining, slides were rinsed twice in PBS and either air dried for 1 hour or incubated with 0.1% Triton X-100 in PBS for 10 min. Cells were blocked in 2% BSA for 30 min, washed, incubated with control IgM or mAb SCH94.03 (10 µg/ml in 1% BSA) for 1 hour, and washed extensively with PBS. After fixation with 4% paraformaldehyde for 15 min, slides were incubated with fluorescein-labeled goat anti-mouse IgM (Jackson Immunoresearch) for 1 hour, washed with PBS, coverslipped with 10% MOWIOL® (Hoechst) in 100 mM Tris, 25% glycerol, pH 8.5 with 25 µg/ml 1,4-diazobicyclo-[2.2.2]-octane (DABCO) to prevent fading, and allowed to set overnight in the dark. For frozen tissue sections, fresh neonatal rat, adult mouse, or autopsied human cortical brain tissue was quick frozen in isopentane chilled in liquid nitrogen prior to liquid nitrogen storage. Frozen sections (10 µm) were transferred onto gelatinized glass microscope slides, air dried for 4–8 hours, and stored at −70° C. Prior to immunostaining, slides were placed at room temperature overnight. The immunoperoxidase staining protocol was similar that described above, using the ABC immunoperoxidase reagent (Vector Laboratories, Burlingame, Calif.), developed with 1.5 mg/ml Hanker-Yates reagent (p-phenylene diamine-procatechol) in 50 mM Tris, pH 7.6 with 0.034% H202, counterstained with Mayer's hematoxylin, and mounted with Permount (Fischer Scientific, Pittsburgh, Pa.).

Data Analysis

A modified cumulative rank sum test (O'Brien, P. C., *Biometrics*, 40:1079–1087 (1984)) was used to compare remyelination between treatment groups. This statistical test takes into account several numerically unrelated parameters of therapeutic effectiveness, and is used routinely for clinical trial efficacy assessment. Parallel analyses using a standard unpaired Student's t-test to compare individual parameters of remyelination gave equivalent results. Comparisons of disease severity and correlation significance were determined by a one-way analysis of variance (ANOVA). Statistical analyses were done with the either the SigmaStat (Jandel Scientific, San Rafael, Calif.) or EXCEL (Microsoft Corporation, Redmond, Wash.) software programs. Calculated values were considered significant when p was <0.05.

Equivalents

Those skilled in the art will recognize, or be able to ascertain, using no more than routine experimentation, many equivalents to the specific embodiments of the invention described herein. Such equivalents are intended to be encompassed by the following claims:

What is claimed is:

1. A monoclonal antibody capable of stimulating remyelination of central nervous system axons, said monoclonal antibody produced by the hybridoma having the ATCC accession No. CRL 11627.

2. A hybridoma consisting of hybridoma ATCC accession No. CRL 11627 that produces a monoclonal antibody capable of stimulating remyelination of central nervous system axons.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 393 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..393

( x i ) SEQUENCE DESCRIPTION: SEQ ID NO:1:

```
ATG ATG TCC TCT GCT CAG TTC CTT GGT CTC CTG TTG CTC TGT TTT CAA      48
Met Met Ser Ser Ala Gln Phe Leu Gly Leu Leu Leu Leu Cys Phe Gln
 1           5                  10                  15

GGT ACC AGA TGT GAT ATC CAG ATG ACA CAG ACT ACA TCC TCC CTG TCT      96
Gly Thr Arg Cys Asp Ile Gln Met Thr Gln Thr Thr Ser Ser Leu Ser
             20                  25                  30

GCC TCT CTG GGA GAC AGA GTC ACC ATC AGT TGC AGG GCA AGT CAG GAC     144
Ala Ser Leu Gly Asp Arg Val Thr Ile Ser Cys Arg Ala Ser Gln Asp
         35                  40                  45

ATT AGC AAT TAT TTA AAC TGG TAT CAG CAG AAA CCA GAT GGA ACT GTT     192
Ile Ser Asn Tyr Leu Asn Trp Tyr Gln Gln Lys Pro Asp Gly Thr Val
     50                  55                  60

AAA CTC CTG ATC TAC TAC ACA TCA AGA TTA CAC TCA GGA GTC CCA TCA     240
Lys Leu Leu Ile Tyr Tyr Thr Ser Arg Leu His Ser Gly Val Pro Ser
 65                  70                  75                  80

AGG TTC AGT GGC AGT GGG TCT GGA ACA GAT TAT TCT CTC ACC ATT AGC     288
Arg Phe Ser Gly Ser Gly Ser Gly Thr Asp Tyr Ser Leu Thr Ile Ser
                 85                  90                  95

AAC CTG GAG CAA GAA GAT ATT GCC ACT TAC TTT TGC CAA CAG GGT AAT     336
Asn Leu Glu Gln Glu Asp Ile Ala Thr Tyr Phe Cys Gln Gln Gly Asn
            100                 105                 110

ACG CTT CCG TGG ACG TTC GGT GGA GGC ACC AAG CTG GAA ATC AAA CGG     384
Thr Leu Pro Trp Thr Phe Gly Gly Gly Thr Lys Leu Glu Ile Lys Arg
        115                 120                 125

GCT GAT GCT                                                          393
Ala Asp Ala
    130
```

( 2 ) INFORMATION FOR SEQ ID NO:2:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Met Ser Ser Ala Gln Phe Leu Gly Leu Leu Leu Leu Cys Phe Gln
 1           5                   10                      15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40              45

Ile Ser Asn Tyr Leu Asn Trp Tyr Gln Gln Lys Pro Asp Gly Thr Val
    50                  55              60

Lys Leu Leu Ile Tyr Tyr Thr Ser Arg Leu His Ser Gly Val Pro Ser
 65             70                  75                      80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105             110

Thr Leu Pro Trp Thr Phe Gly Gly Gly Thr Lys Leu Glu Ile Lys Arg
        115                 120             125

Ala Asp Ala
    130
```

(2) INFORMATION FOR SEQ ID NO:3:

(i) SEQUENCE CHARACTERISTICS:
        (A) LENGTH: 324 base pairs
        (B) TYPE: nucleic acid
        (C) STRANDEDNESS: double
        (D) TOPOLOGY: linear (xi) SEQUENCE DESCRIPTION: SEQ ID NO:3:

```
GATATCCAGA TGACACAGAC TACATCCTCC CTGTCTGCCT CTCTGGGAGA CAGAGTCACC    60
ATCAGTTGCA GGGCAAGTCA GGACATTAGC AATTATTTAA ACTGGTATCA GCAGAAACCA   120
GATGGAACTG TTAAACTCCT GATCTACTAC ACATCAAGAT TACACTCAGG AGTCCCATCA   180
AGGTTCAGTG GCAGTGGGTC TGGAACAGAT TATTCTCTCA CCATTAGCAA CCTGGAGCAA   240
GAAGATATTG CCACTTACTT TTGCCAACAG GGTAATACGC TTCCTCCGAC GTTCGGTGGA   300
GGCACCAAGC TGGAAATCAA ACGG                                          324
```

(2) INFORMATION FOR SEQ ID NO:4:

(i) SEQUENCE CHARACTERISTICS:
        (A) LENGTH: 285 base pairs
        (B) TYPE: nucleic acid
        (C) STRANDEDNESS: double
        (D) TOPOLOGY: linear (xi) SEQUENCE DESCRIPTION: SEQ ID NO:4:

```
GATATCCAGA TGACACAGAC TACATCCTCC CTGTCTGCCT CTCTGGGAGA CAGAGTCACC    60
ATCAGTTGCA GGGCAAGTCA GGACATTAGC AATTATTTAA ACTGGTATCA GCAGAAACCA   120
GATGGAACTG TTAAACTCCT GATCTACTAC ACATCAAGAT TACACTCAGG AGTCCCATCA   180
AGGTTCAGTG GCAGTGGGTC TGGAACAGAT TATTCTCTCA CCATTAGCAA CCTGGAGCAA   240
GAAGATATTG CCACTTACTT TTGCCAACAG GGTAATACGC TTCCT                   285
```

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: double
        (D) TOPOLOGY: linear ( x i ) SEQUENCE DESCRIPTION: SEQ ID NO:5:

TGGACGTTCG GTGGAGGCAC CAAGCTGGAA ATCAAACGT    39

( 2 ) INFORMATION FOR SEQ ID NO:6:

( i ) SEQUENCE CHARACTERISTICS:
        ( A ) LENGTH: 429 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..429

( x i ) SEQUENCE DESCRIPTION: SEQ ID NO:6:

```
ATG  GGA  TGG  AGC  TGT  ATC  ATC  CTC  TTT  TTG  GTA  GCA  GCA  GCT  ACA  GGT      48
Met  Gly  Trp  Ser  Cys  Ile  Ile  Leu  Phe  Leu  Val  Ala  Ala  Ala  Thr  Gly
 1              5                        10                       15

GTC  CAC  TCC  CAG  GTC  CAA  CTG  CAG  CAG  CCT  GGG  ACT  GAA  CTG  GTG  AAG      96
Val  His  Ser  Gln  Val  Gln  Leu  Gln  Gln  Pro  Gly  Thr  Glu  Leu  Val  Lys
             20                       25                       30

CCT  GGG  GCT  TCA  GTG  AAG  CTG  TCC  TGC  AAG  GCT  TCT  GGC  TAC  ACC  TTC     144
Pro  Gly  Ala  Ser  Val  Lys  Leu  Ser  Cys  Lys  Ala  Ser  Gly  Tyr  Thr  Phe
             35                       40                       45

ACC  AGC  TAC  TGG  ATG  CAC  TGG  GTG  AAG  CAG  AGG  CCT  GGA  CAA  GGC  CTT     192
Thr  Ser  Tyr  Trp  Met  His  Trp  Val  Lys  Gln  Arg  Pro  Gly  Gln  Gly  Leu
         50                       55                       60

GAG  TGG  ATT  GGA  AAT  ATT  AAT  CCT  AGC  AAT  GGT  GGT  ACT  AAC  TAC  AAT     240
Glu  Trp  Ile  Gly  Asn  Ile  Asn  Pro  Ser  Asn  Gly  Gly  Thr  Asn  Tyr  Asn
 65                       70                       75                       80

GAG  AAG  TTC  AAG  AGC  AAG  GCC  ACA  CTG  ACT  GTA  GAC  AAA  TCC  TCC  AGC     288
Glu  Lys  Phe  Lys  Ser  Lys  Ala  Thr  Leu  Thr  Val  Asp  Lys  Ser  Ser  Ser
                      85                       90                       95

ACA  GCC  TAC  ATG  CAG  CTC  AGC  AGC  CTG  ACA  TCT  GAG  GAC  TCT  GCG  GTC     336
Thr  Ala  Tyr  Met  Gln  Leu  Ser  Ser  Leu  Thr  Ser  Glu  Asp  Ser  Ala  Val
                100                      105                      110

TAT  TAT  TAT  GCA  AGA  CGG  GCC  CCT  TAC  TAC  GGT  AGT  AGG  AAC  TTT  GAC     384
Tyr  Tyr  Tyr  Ala  Arg  Arg  Ala  Pro  Tyr  Tyr  Gly  Ser  Arg  Asn  Phe  Asp
            115                      120                      125

TAC  TGG  GGC  CAA  GGC  ACC  ACT  CTC  ACA  GTC  TCC  TCA  GAG  AGT  CAG          429
Tyr  Trp  Gly  Gln  Gly  Thr  Thr  Leu  Thr  Val  Ser  Ser  Glu  Ser  Gln
        130                      135                      140
```

( 2 ) INFORMATION FOR SEQ ID NO:7:

( i ) SEQUENCE CHARACTERISTICS:
        ( A ) LENGTH: 143 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Gly  Trp  Ser  Cys  Ile  Ile  Leu  Phe  Leu  Val  Ala  Ala  Ala  Thr  Gly
 1              5                        10                       15

Val  His  Ser  Gln  Val  Gln  Leu  Gln  Gln  Pro  Gly  Thr  Glu  Leu  Val  Lys
             20                       25                       30

Pro  Gly  Ala  Ser  Val  Lys  Leu  Ser  Cys  Lys  Ala  Ser  Gly  Tyr  Thr  Phe
             35                       40                       45

Thr  Ser  Tyr  Trp  Met  His  Trp  Val  Lys  Gln  Arg  Pro  Gly  Gln  Gly  Leu
         50                       55                       60

Glu  Trp  Ile  Gly  Asn  Ile  Asn  Pro  Ser  Asn  Gly  Gly  Thr  Asn  Tyr  Asn
```

| | | | | | 65 | | | | 70 | | | | 75 | | | | 80 |
|---|---|---|---|---|---|---|---|---|---|---|---|---|---|---|---|---|---|
| Glu | Lys | Phe | Lys | Ser | Lys | Ala | Thr | Leu | Thr | Val | Asp | Lys | Ser | Ser | Ser |
| | | | | 85 | | | | | 90 | | | | | 95 | |

Thr Ala Tyr Met Gln Leu Ser Ser Leu Thr Ser Glu Asp Ser Ala Val
                100                     105                     110

Tyr Tyr Tyr Ala Arg Arg Ala Pro Tyr Tyr Gly Ser Arg Asn Phe Asp
            115                 120                 125

Tyr Trp Gly Gln Gly Thr Thr Leu Thr Val Ser Ser Glu Ser Gln
        130             135                 140

( 2 ) INFORMATION FOR SEQ ID NO:8:

( i ) SEQUENCE CHARACTERISTICS:
        ( A ) LENGTH: 366 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..366

( x i ) SEQUENCE DESCRIPTION: SEQ ID NO:8:

```
CAG  GTC  CAA  CTG  CAG  CAG  CCT  GGG  ACT  GAA  CTG  GTG  AAG  CCT  GGG  GCT       48
Gln  Val  Gln  Leu  Gln  Gln  Pro  Gly  Thr  Glu  Leu  Val  Lys  Pro  Gly  Ala
 1                    5                        10                       15

TCA  GTG  AAG  CTG  TCC  TGC  AAG  GCT  TCT  GGC  TAC  ACC  TTC  ACC  AGC  TAC       96
Ser  Val  Lys  Leu  Ser  Cys  Lys  Ala  Ser  Gly  Tyr  Thr  Phe  Thr  Ser  Tyr
               20                        25                       30

TGG  ATG  CAC  TGG  GTG  AAG  CAG  AGG  CCT  GGA  CAA  GGC  CTT  GAG  TGG  ATT      144
Trp  Met  His  Trp  Val  Lys  Gln  Arg  Pro  Gly  Gln  Gly  Leu  Glu  Trp  Ile
          35                        40                       45

GGA  AAT  ATT  AAT  CCT  AGC  AAT  GGT  GGT  ACT  AAC  TAC  AAT  GAG  AAG  TTC      192
Gly  Asn  Ile  Asn  Pro  Ser  Asn  Gly  Gly  Thr  Asn  Tyr  Asn  Glu  Lys  Phe
     50                        55                       60

AAG  AGC  AAG  GCC  ACA  CTG  ACT  GTA  GAC  AAA  TCC  TCC  AGC  ACA  GCC  TAC      240
Lys  Ser  Lys  Ala  Thr  Leu  Thr  Val  Asp  Lys  Ser  Ser  Ser  Thr  Ala  Tyr
 65                      70                       75                       80

ATG  CAG  CTC  AGC  AGC  CTG  ACA  TCT  GAG  GAC  TCT  GCG  GTC  TAT  TAT  TAT      288
Met  Gln  Leu  Ser  Ser  Leu  Thr  Ser  Glu  Asp  Ser  Ala  Val  Tyr  Tyr  Tyr
               85                        90                       95

GCA  AGA  GAT  TAC  TAC  GGT  AGT  AGC  TGG  GGG  TAC  TAC  TTT  GAC  TAC  TGG      336
Ala  Arg  Asp  Tyr  Tyr  Gly  Ser  Ser  Trp  Gly  Tyr  Tyr  Phe  Asp  Tyr  Trp
          100                       105                      110

GGC  CAA  GGC  ACC  ACT  CTC  ACA  GTC  TCC  TCA                                    366
Gly  Gln  Gly  Thr  Thr  Leu  Thr  Val  Ser  Ser
     115                      120
```

( 2 ) INFORMATION FOR SEQ ID NO:9:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

Gln Val Gln Leu Gln Gln Pro Gly Thr Glu Leu Val Lys Pro Gly Ala
 1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile

|   |   | 35 |   |   |   | 40 |   |   |   | 45 |   |   |
|---|---|---|---|---|---|---|---|---|---|---|---|---|
| Gly | Asn 50 | Ile | Asn | Pro | Ser | Asn 55 | Gly | Gly | Thr | Asn | Tyr 60 | Asn Glu Lys Phe |

Lys Ser Lys Ala Thr Leu Thr Val Asp Lys Ser Ser Ser Thr Ala Tyr
65              70                  75                      80

Met Gln Leu Ser Ser Leu Thr Ser Glu Asp Ser Ala Val Tyr Tyr Tyr
              85                  90                  95

Ala Arg Asp Tyr Tyr Gly Ser Ser Trp Gly Tyr Tyr Phe Asp Tyr Trp
            100             105                 110

Gly Gln Gly Thr Thr Leu Thr Val Ser Ser
        115             120

(2) INFORMATION FOR SEQ ID NO:10:

(i) SEQUENCE CHARACTERISTICS:
      (A) LENGTH: 351 base pairs
      (B) TYPE: nucleic acid
      (C) STRANDEDNESS: double
      (D) TOPOLOGY: linear (xi) SEQUENCE DESCRIPTION: SEQ ID NO:10:

ATGGGATGGA GCTGTATCAT CCTCTTTTTG GTAGCAGCAG CTACAGGTGT CCACTCCCAG      60

GTCCAACTGC AGCAGCCTGG GACTGAACTG GTGAAGCCTG GGGCTTCAGT GAAGCTGTCC     120

TGCAAGGCTT CTGGCTACAC CTTCACCAGC TACTGGATGC ACTGGGTGAA GCAGAGGCCT     180

GGACAAGGCC TTGAGTGGAT TGGAAATATT AATCCTAGCA ATGGTGGTAC TAACTACAAT     240

GAGAAGTTCA AGAGCAAGGC CACACTGACT GTAGACAAAT CCTCCAGCAC AGCCTACATG     300

CAGCTCAGCA GCCTGACATC TGAGGACTCT GCGGTCTATT ATTATGCAAG A             351

(2) INFORMATION FOR SEQ ID NO:11:

(i) SEQUENCE CHARACTERISTICS:
      (A) LENGTH: 45 base pairs
      (B) TYPE: nucleic acid
      (C) STRANDEDNESS: double
      (D) TOPOLOGY: linear (xi) SEQUENCE DESCRIPTION: SEQ ID NO:11:

TACTTTGACT ACTGGGGCCA AGGCACCACT CTCACAGTCT CCTCA                      45